(12) United States Patent
Friedman et al.

(10) Patent No.: US 12,186,435 B2
(45) Date of Patent: Jan. 7, 2025

(54) SOL-GEL/HYDROGEL THERAPEUTIC DELIVERY SYSTEM AND METHODS THEREOF

(71) Applicant: ALBERT EINSTEIN COLLEGE OF MEDICINE, Bronx, NY (US)

(72) Inventors: Joel Friedman, West Orange, NJ (US); Andrew Draganski, Greenville, SC (US); Adam Friedman, Bethesda, MD (US); Mahantesh Navati, Bronx, NY (US); Parimala Nacharaju, Staten Island, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 16/484,680

(22) PCT Filed: Feb. 9, 2018

(86) PCT No.: PCT/US2018/017524
§ 371 (c)(1),
(2) Date: Aug. 8, 2019

(87) PCT Pub. No.: WO2018/148475
PCT Pub. Date: Aug. 16, 2018

(65) Prior Publication Data
US 2020/0030247 A1 Jan. 30, 2020

Related U.S. Application Data

(60) Provisional application No. 62/457,405, filed on Feb. 10, 2017.

(51) Int. Cl.
| | | |
|---|---|---|
| A61K 9/51 | (2006.01) | |
| A61K 9/19 | (2006.01) | |
| A61K 31/12 | (2006.01) | |
| A61K 31/198 | (2006.01) | |
| A61K 33/00 | (2006.01) | |
| A61K 47/69 | (2017.01) | |
| B01J 13/00 | (2006.01) | |

(52) U.S. Cl.
CPC .............. *A61K 9/5192* (2013.01); *A61K 9/19* (2013.01); *A61K 31/12* (2013.01); *A61K 31/198* (2013.01); *A61K 33/00* (2013.01); *A61K 47/6929* (2017.08); *B01J 13/0065* (2013.01)

(58) Field of Classification Search
None
See application file for complete search history.

(56) References Cited

U.S. PATENT DOCUMENTS

| | | |
|---|---|---|
| 7,439,272 B2 | 10/2008 | Dengfeng |
| 10,028,918 B2 | 7/2018 | Nacharaju et al. |
| 2006/0131238 A1* | 6/2006 | Xu ..................... B01J 20/28057 210/656 |
| 2012/0183593 A1* | 7/2012 | Schultz .................. A61K 38/28 514/169 |
| 2012/0213697 A1* | 8/2012 | Friedman ............... A61K 45/06 424/1.25 |
| 2015/0147396 A1* | 5/2015 | Nacharaju ............ A61K 31/095 424/489 |

FOREIGN PATENT DOCUMENTS

WO 20160094189 A1 6/2016

OTHER PUBLICATIONS

Aerogel (http://www.aerogel.org/?p=1406 (2010) (Year: 2010).*
Brinker1 (Sol-gel transition in simple silicates II. Journal of Non-Crystalline Solids 63 (1984) 45-59) (Year: 1984).*
Brinker2 et al (Sol-Gel Science: The Physics and Chemistry of Sol-Gel Processing. Academic Press, Inc (1990) p. 1-908; see IDS filed on Oct. 24, 2019, wherein Chapter 6: Aging of Gels in the book is provided) (Year: 1990).*
Brinker, et al. "Sol-Gel Science: The Physics and Chemistry of Sol-Gel Processing" *Academic Press, Inc.* (1990) pp. 1-908. https://books.google.com/books?id=CND1BAAAQBAJ&lpg=PP1&ots=aezJC1ZcdF&dq=Brinker%2C%20C.J.%20and%20Scherer%2C%20G.W.%20%20Sol-Gel%20Science.%20%20The%20Physics%20and%20Chemistry%20of%20Sol-Gel%20Processing.%20%20Academic%20Press%2C%20Inc.%201990&lr&pg=PP1#v=onepage&q&f=false (Web only).
Buchwald, et al. "Long-term, continuous intravenous heparin administration by an implantable infusion pump in ambulatory patients with recurrent venous thrombosis" *Surgery* 88(4) (1980) pp. 507-516. (Abstract only).
During, et al. "Controlled release of dopamine from a polymeric brain implant: In vivo characterization" *Ann. Neurol.* 25 (1989) pp. 351-356.
Goodson, J.M. "Dental Applications" *Medical Applications of Controlled Release*—vol. 2 (1984) pp. 115-138.
Howard, et al. "Intracerebral drug delivery in rats with lesion-induced memory deficits" *J. Neurosurg.* 71 (1989) pp. 105-112. (Abstract only).
Langer, R. "New Methods of Drug Delivery" *Science* 249 (1990) pp. 1527-1533. (Abstract only).
Langer, et al. "Chemical and Physical Structure of Polymers as Carriers for Controlled Release of Bioactive Agents: A Review" *J. Macromol. Sci. Pt. C—Polym. Rev.* 23 (1983) pp. 61-126. (Abstract only).
Langer, et al. "Medical Applications of Controlled Release" *CRC Press* (1974).
Levy, et al. "Inhibition of calcification of bioprosthetic heart valves by local controlled-release diphosphonate" *Science* 228(4696) (1985) pp. 190-192. (Abstract only).
Martin, et al. "Remington's Pharmaceutical Sciences" *Mack Publishing Co.* (1965).

(Continued)

*Primary Examiner* — Jake M Vu
(74) *Attorney, Agent, or Firm* — Maynard Nexsen PC; John P. Zimmer

(57) ABSTRACT

Disclosed herein is a delivery platform for the preparation of versatile sol-gel/hydrogel based nano and micro particles that can be loaded with small molecules. The delivery platform is suitable for topical, transdermal, IV, IP and aerosol drug delivery. Also disclosed herein are methods of treatment using the aforementioned particles.

22 Claims, 18 Drawing Sheets

(56) References Cited

OTHER PUBLICATIONS

Saudek, et al. "A Preliminary Trial of the Programmable Implantable Medication System for Insulin Delivery" *N. Engl. J. Med.* 321 (1989) pp. 574-579. (Abstract only).
Sefton, M.V. "Implantable Pumps" *Crit. Rev. Biomed. Eng.* 14(3) (1987) pp. 201-240. (Abstract only).
Smolen, et al. "Drug Product Design and Performance" *Wiley-Interscience* (1984).
ISA PCT International Search Report & Written Opinion, PCT/US2018/017524 (May 4, 2018) pp. 1-8.
Hoang Geun Chang et al. "Pore Size Control of Silica Gels in Basic Water Conditions Using Sol-Gel Processing", Proceedings of the 5th International Conference on Properties and Applications of Dielectric Materials May 25-30, 1997, Seoul, Korea, IEEE, May 25, 1997, vol. 1, pp. 174-177, 4 pages.
Kwon Sooyeon et al. "Silica-based mesoporous nanoparticles for controlled drug delivery", Journal of Tissue Engineering, Jan. 1, 2013, 18 pages.
Examination Report corresponding to Australian Patent App No. 2018219908, mailed Aug. 13, 2024, 5 pages.

\* cited by examiner

SOL-GEL/HYDROGEL THERAPEUTIC DELIVERY SYSTEM AND METHODS THEREOF

CROSS-REFERENCE TO RELATED APPLICATION

This application claims the benefit of U.S. Provisional Application No. 62/457,405, filed Feb. 10, 2017, the contents of which is hereby incorporated by reference.

INTRODUCTION

Disclosed herein is a delivery platform for the preparation of versatile sol-gel/hydrogel based nano and micro particles that can be loaded with small molecules. The delivery platform is suitable for topical, transdermal, IV, IP and aerosol drug delivery.

Also disclosed herein are methods of treatment using the aforementioned particles.

BACKGROUND

There is a need for approaches to targeted drug delivery that increase the amount of drug delivered to the targeted site without increasing the amount of administered drug, as well as minimizing systemic toxicity of the drug delivered.

SUMMARY OF THE INVENTION

Disclosed herein is a method for preparing versatile small molecule delivery platforms suitable for topical, transdermal, IV, IP and aerosol drug delivery. The basic steps for preparing these materials is as follows.

Blank silane-derived sol-gel blocks are prepared using the Brinker methodology. The basic sol-gel/hydrogel monoliths are created in two steps: an initial hydrolysis of the starting silanes followed by a condensation reaction that produces the polymeric network that comprises the sol-gel. The basic recipe utilizes tetramethoxy silane (TMOS) or other similar tetra substituted silanes such as tetraethoxysilane (TEMOS). Hydrolyzed TMOS can be mixed with other hydrolyzed silanes such as X-trimethoxy silanes (where X can be a wide variety of side chains attached to the Si group including: thiols, amines, alkyl chains, fatty acids, carboxy groups, carbonyl groups, PEG chains, sugars, starches, peptides). The hydrolyzed mix is then allowed to undergo the condensation reaction to create the monolith sol-gel. The mixing of the two hydrolyzed populations allows for the doping of the polymeric network with the X side chains that have become incorporated into the polymer.

The blank sol-gels are then loaded with the desired deliverable by introducing onto the sol-gel a suitably concentrated solution of the deliverable in a solvent that can be removed through lyophilization. Aqueous and non-aqueous solvents can be used to load the deliverable depending on the solubility properties of the deliverable.

Once the sol-gel has been appropriately loaded with the deliverable, the sol-gel is then lyophilized until the material appears fully dry/desiccated. All solvent (e.g., alcohol or water) is removed through this step.

The resulting dry material is then ball milled or jet milled which produces a fine powder comprised largely of micron sized particles with a contribution of submicron particles the dimensions of and percent content of depends upon the mode of milling.

The dry milled powder can then be wet milled which yields a narrow distribution of particles with a peak distribution in 100 to 200 nanometer diameter regime.

The dry particles can also be wet ground using a mortar and pestle to generate intermediate sized particles.

Resulting materials can be stored in a suitable freezer for extended periods without any obvious loss of efficacy or content.

DEFINITIONS

Figure 1:
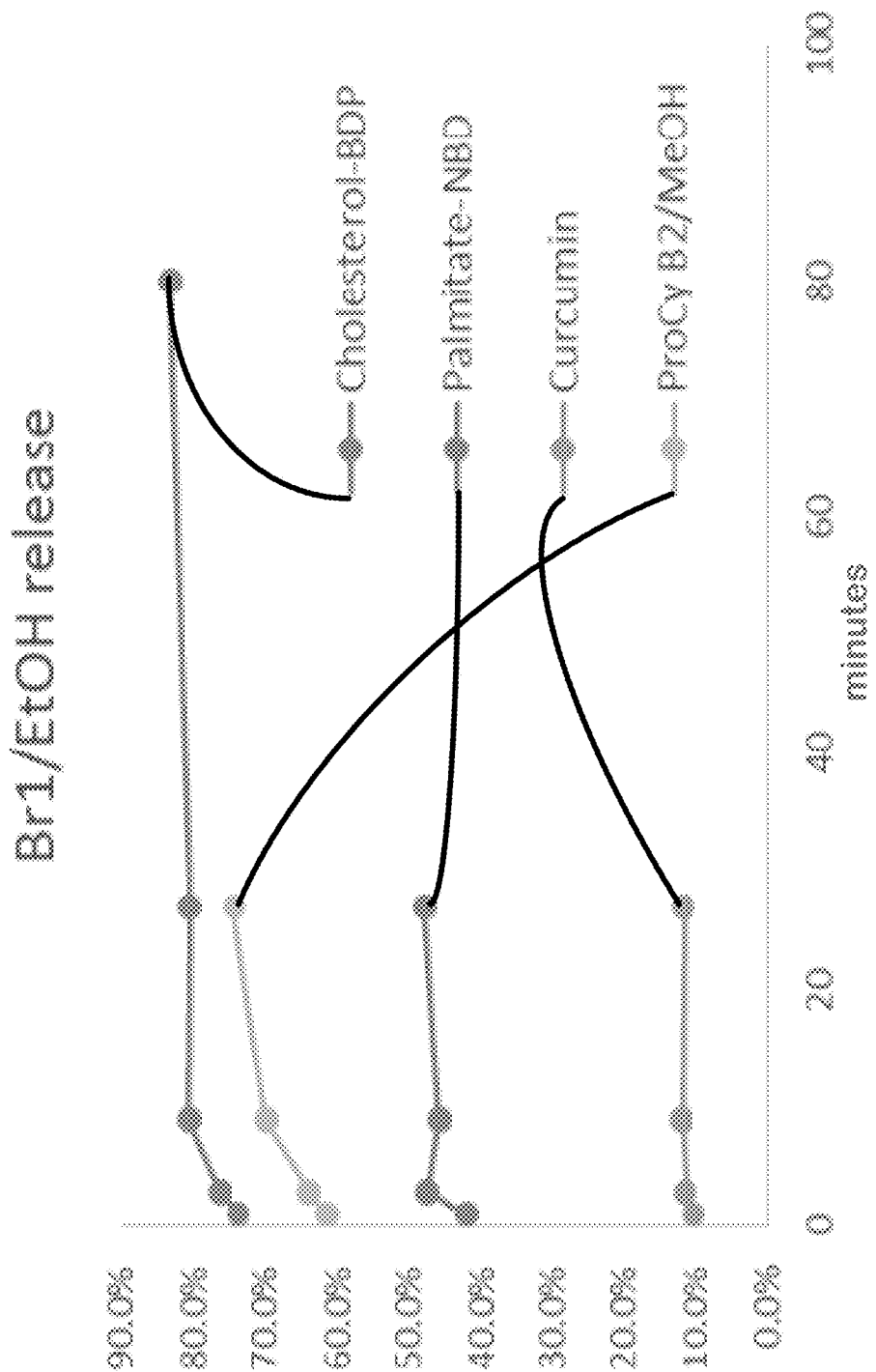
FIG. 1. Loading of hydrophobic compounds using Brinker 1 protocol. Plots from top to bottom, respectively: Cholesterol-BDP, ProCy B2/MeOH, Palmitate-NBD, and Curcumin.

When referring to the compounds and methods provided herein, the following terms have the following meanings unless otherwise indicated.

As used herein, a "hydrogel" is a sol-gel that has not undergone extensive drying. In contrast, a xerogel is a sol-gel that has undergone extensive drying. The terms hydrogel and sol-gel are used interchangeably in this application.

As used herein, "Brinker" chemistry, method, methodology, process and protocol refer to the chemistry and process set forth in Brinker, C. J. and Scherer, G. W. Sol-Gel Science. The Physics and Chemistry of Sol-Gel Processing. Academic Press, Inc. 1990.

As used herein, the term "agent" refers to any molecule, compound, and/or substance for use in the prevention, treatment, management and/or diagnosis of a disease, including but not limited to cancer.

As used herein, the term "amount," as used in the context of the amount of a particular cell population or cells, refers to the frequency, quantity, percentage, relative amount, or number of the particular cell population or cells.

As used herein, the term "bind" or "bind(s)" refers to any interaction, whether direct or indirect, that affects the specified receptor (target) or receptor (target) subunit.

As used herein, the terms "disorder" and "disease" are used interchangeably to refer to a pathological condition in a subject.

As used herein, the term "effective amount" refers to the amount of a therapy that is sufficient to result in the prevention of the development, recurrence, or onset of a disease and one or more symptoms thereof, to enhance or improve the prophylactic effect(s) of another therapy, reduce the severity, the duration of a disease, ameliorate one or more symptoms of a disease, prevent the advancement of a disease, cause regression of a disease, and/or enhance or improve the therapeutic effect(s) of another therapy.

As used herein, the phrase "elderly human" refers to a human 65 years old or older, preferably 70 years old or older.

As used herein, the phrase "human adult" refers to a human 18 years of age or older.

As used herein, the phrase "human child" refers to a human between 24 months of age and 18 years of age.

As used herein, the phrase "human infant" refers to a human less than 24 months of age, preferably less than 12 months of age, less than 6 months of age, less than 3 months of age, less than 2 months of age, or less than 1 month of age.

As used herein, the term "in combination" in the context of the administration of a therapy to a subject refers to the use of more than one therapy (e.g., prophylactic and/or therapeutic). The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to a disease or disorder. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the terms "manage," "managing," and "management" in the context of the administration of a therapy to a subject refer to the beneficial effects that a subject derives from a therapy (e.g., a prophylactic or therapeutic agent) or a combination of therapies, while not resulting in a cure of a disease or disorder. In certain embodiments, a subject is administered one or more therapies (e.g., one or more prophylactic or therapeutic agents) to "manage" a disease or disorder so as to prevent the progression or worsening of the condition.

As used herein, the phrase "pharmaceutically acceptable" means approved by a regulatory agency of the federal or a state government, or listed in the United States Pharmacopeia, European Pharmacopeia, or other generally recognized pharmacopeia for use in animals, and more particularly, in humans.

In certain embodiments, the compositions comprising the disclosed particles are administered to a patient, preferably a human, as a preventative measure against such diseases. As used herein, "prevention" or "preventing" refers to a reduction of the risk of acquiring a given disease or disorder. In a preferred mode of the embodiment, the compositions comprising the modified nanoparticles are administered as a preventative measure to a patient, preferably a human, having a genetic predisposition to the above identified conditions. In another preferred mode of the embodiment, the compositions comprising the modified nanoparticles are administered as a preventative measure to a patient having a non-genetic predisposition to the above-identified conditions.

As used herein, the terms "purified" and "isolated" when used in the context of a compound or agent (including proteinaceous agents such as antibodies) that can be obtained from a natural source, e.g., cells, refers to a compound or agent that is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells.

As used herein, the phrase "small molecule(s)" and analogous terms include, but are not limited to, peptides, peptidomimetics, amino acids, amino acid analogs, polynucleotides, polynucleotide analogs, nucleotides, nucleotide analogs, and other organic and inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

In at least one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

Concentrations, amounts, cell counts, percentages, and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

The term "about" as used herein refers to ±5% of the reference value.

DETAILED DESCRIPTION OF THE INVENTION

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill in the art have not been described in detail so as not to obscure claimed subject matter. It is to be understood that particular features, structures, or characteristics described may be combined in various ways in one or more implementations.

In general, the present application relates to the preparation and administration of disclosed nanoparticles and/or pharmaceutical compositions comprising the nanoparticles. In one or more embodiments, methods of preparing modified nanoparticles and/or pharmaceutical compositions comprising modified nanoparticles are provided. In one or more embodiments, methods of treating or preventing or managing a disease or disorder in humans by administering a pharmaceutical composition comprising an amount of modified nanoparticles are provided. Also provided herein is a method of treatment comprising administering to the subject an effective amount of one or more of the nanoparticles disclosed herein and a pharmaceutically acceptable carrier. Further, provided herein is a pharmaceutical composition comprising any of the nanoparticles disclosed herein and a pharmaceutically acceptable carrier.

In certain embodiments, the modified nanoparticles comprise 10-20, 20-30, 30-40, 40-50, 50-60, 60-70, 70-80, 80-90, 90-100 µg of therapeutic agent per mg of nanoparticle. In certain embodiments, the modified nanoparticles comprise 22-44, 24-40, 50-60 µg of therapeutic agent per mg of nanoparticle.

In certain embodiments, the modified nanoparticles comprise 10-20, 20-30, 30-40, 40-50, 50-60, 60-70, 70-80, 80-90, 90-100 µg of therapeutic agent per mg of nanoparticle per unit time. In certain embodiments, the modified nanoparticles comprise 22-44, 24-40, 50-60 µg of therapeutic agent per mg of nanoparticle per unit time. In certain embodiment, the unit time is 1-5, 5-10, 10-15, 15-20, 20-25, 25-30, 30-35, 35-40, 40-45, 45-50, 50-60 secs, 1-2 mins, 2-5 mins, 5-10 mins, 10-30 mins, 30-60 mins.

In certain embodiments, the modified nanoparticles have a core size of 50-60, 60-70, 70-80, 80-90, 90-100, 100-110, 110-120, 120-130, 130-140, 140-150, 150-160, 160-170, 170-180, 180-190, 190-200, 200-300, 300-400, and 400-500 nm. In certain embodiment, modified nanoparticles have a core size of 70-150 nm.

In certain embodiments, the modified nanoparticles comprise 2, 3, 4, 5, 6, 7, 8, 9, 10, 20, 30, 40, 50 folds more therapeutic agents than nanoparticles that do not have the modification(s) described in the present disclosure.

In certain embodiments, the modified nanoparticles as disclosed herein have improved permeability crossing the blood brain barrier as compared to other nanoparticles having similar size. In certain embodiments, the modified nanoparticles have a nanoparticle core that has similar size as other previously known nanoparticles and yet has an increased permeability crossing the blood brain barrier by the order of at least 10, $10\text{-}10^2$, $10^2\text{-}10^3$, $10^3\text{-}10^4$, $10^4\text{-}10^5$. In certain embodiments, the modified nanoparticles are 2, 3, 4, 5, 6, 7, 8, 9, 10, 20, 30, 40, 50 folds more efficient in penetration across the blood brain barrier than nanoparticles that does not have the modification(s) described in the present disclosure.

In certain embodiments, the modified nanoparticles are 2, 3, 4, 5, 6, 7, 8, 9, 10, 20, 30, 40, 50 folds more efficient in entering a cell at the location that the nanoparticles are targeted in a subject than nanoparticles that do not have the modification(s) described in the present disclosure. In certain embodiments, the cells are cancer cells. In certain embodiments, the cells are glioblastoma cells. In certain embodiments, the cells are cardiac cells, blood vessel cells and capillary cells. In certain embodiments, the cells are bone marrow, spleen, brain, bone, etc.

In certain embodiments, the modified nanoparticles have a size dispersion of 0-5%, 5-15%, 15-20%, 20-25% and 25-30%. In certain embodiments, the modified nanoparticles have a size dispersion of less than 1%. In certain embodiments, the modified nanoparticles have a size dispersion of less than 0.1%.

In certain embodiments, the modified nanoparticles of the present application can be formed in sizes having a diameter in dry form, for example, of 80 nm to 1000 µm, preferably 80 nm to 200 µm, or 80 nm to 1 µm, or 80 nm to 500 nm, or 80 nm to 100 nm. Preferably, the nanoparticles have an average diameter of less than 500 nm.

Sol-gel/Hydrogel Based Nanoparticles

The blank sol-gels can be loaded with virtually any small (non-protein) molecule including both hydrophilic and hydrophobic/lipophilic molecules using either aqueous or non-aqueous solvents to introduce the molecule into the gel.

Examples include, but are not limited to: S-nitrosothiol and thiol containing small molecules, Glutathione (GSH) and S-nitrosothiol-GSH (GSNO), N-acetylcysteine (NAC) and NACSNO, S-nitroso-N-acetylpenicillamine (SNAP), Curcumin, siRNA, cholesterol, palmitic acid, Evans Blue (dye), Naproxin, Peptides, PDE5 inhibitors, Nitrite and Ascorbic acid.

The polymeric network comprising the sol-gel determines the release rate of the deliverables from the resulting nano/micro particles. The polymeric network created during the gelation process for the sol-gel determines how narrow or large are pores within the sol-gel through which the loaded deliverable must traverse to escape from the final nano/micro particle. The gelation or condensation process (polymeric structure) determines the size distribution of the pores within the sol-gel. It can be easily tuned using pH, dopants, ratio of water to alcohol.

The initial hydrolysis process is carried out under low water conditions which favors the formation of a substantial population of silanes having only one of four sites hydrolyzed. This hydrolyzed starting material allows for a choice of next step condensation conditions that covers both rapid and slow condensation/polymerization which in turn determines the pore size and release rates for final particles.

In general, slow condensation/gelation is favored by lower pH values for the added aqueous buffer used to initiate condensation/gelation. Slow condensation favors the smallest pores which results in slower release rates of the loaded deliverable. Particles made through this process as disclosed herein are sometimes referred to as Br1 particles. The Br refers to the Brinker method.

Fast gelation is favored by higher pH resulting in larger pores which produces particles manifesting faster release profiles. Particles made through this approach as disclosed herein are referred to as Br2 or Br3 particles.

Dopants that disrupt the linear polymeric network created using the low pH conditions (Br1) can result in enhanced release rates compared to the undoped Br1 particles. Dopants added to the initial sol mixture prior to gelation can be used both to modify drug release profiles and modify surface properties of the resulting nano/micro particles By manipulating the charge within the polymeric network, it can be used to slow the release of charged molecules. Sol-gels doped with amine containing silanes (e.g., APTS) result in a dramatic slowdown in the release profile of negatively charged water soluble dye (e.g., Evans Blue which contains four sulfonates) from the resulting nano/micro particles.

Addition of small PEG chains (PEG200 or PEG400) results in enhanced levels of NO released from SNOnp due at least in part to stabilization of the covalently attached SNO moieties within the resulting SNOnp/SNOmp. Doping with silanes containing long alkyl chains slow release of hydrophobic molecules. Doping with silanes containing reactive groups such amines or thiols allow for the covalent attachment of small and large molecules such as different derivatized PEG chains to the surface of the nano/micro particles thus allowing for: (i) improved circulation lifetimes within the vasculature; (ii) PEGylation creates a stealth particle that is not recognized by the immune system; (iii) improved suspension properties; (iv) attachment of dye molecules (via fluorescent PEG); and (v) attachment of tissue targeting molecules including antibodies and peptides either directly on the surface or via a linker such as a derivatized PEG chain.

As described herein, a platform has been developed for the preparation of Sol-gel/hydrogel-based nanoparticles. In certain embodiments, the nanoparticles can be loaded with therapeutic agents including, but not limited to: drugs (e.g. chemotherapeutics), nutraceuticals (e.g. curcumin), peptides, thiol-containing small molecules, anti-inflammatories, nitric oxide (NO), NO precursors, nitrosothiols, NACSNO (the S-nitrosothiol derivative of N-acetyl cysteine), imaging agents (MRI, CT, PET, fluorescence), melanin, plasmids, tadalafil, doxorubicin, siRNA, plasmids, nitro fatty acids, and salts and ions (metal and rare earth). In one or more embodiments, the nanoparticles can be coated with PEG including derivatized PEG and/or cell or tissue targeting molecules. The nanoparticles can be used for both topical and systemic applications. In one or more embodiments, the nanoparticles can form a very fine powder when dry and a uniform suspension when added to liquid solvents (e.g., water, alcohol, DMSO).

Disclosed herein is a drug delivery platform that can be prepared with tuned physical and functional the properties of the sol-gel independent of the loaded deliverables. Whereas other delivery platforms require that the deliverable be present in the initial reaction mix and as a consequence, the deliverable can impact the properties of the resulting materials. For example, a silane-derived nanoparticle platform required mixing the deliverable into the starting mixture which precluded facile and systematic tuning of pore structure/release rates as well as limiting the deliverables to molecules that could withstand the gelation process.

The present delivery platform also has the advantage in that multiple deliverables can be loaded into the same sol-gel block.

In one embodiment, the properties of the sol-gel which influence release rates are tuned independent of the deliverable.

The same platform can accommodate a myriad of deliverables whereas other such approaches require modifying the formulation and preparative protocol for each deliverable and indication.

In one embodiment, unstable deliverables can now be loaded without concern for degradation during the condensation/gelation process. For example, if low pH or high temperature is required to generate the hydrogel with the appropriate physical properties, it would not be possible to introduce a pH or temperature sensitive deliverable prior to the condensation reaction that yields the hydrogel.

In one embodiment, slow release requires low pH gelation conditions which would lead to degradation of many deliverables if loaded prior to gelation.

Size distribution is determined by mechanical processing and not subtle and often complex chemistry/physics related processes. This feature allows for the focusing on optimizing loading, release rates, post production surface modifications without the added complexity of dealing with the chemistry and physics that can dramatically alter size distribution.

The preparation of ultimate drug delivery platform (UDDP) particles consists of the following steps: hydrolysis, condensation, loading the deliverable, drying (lyophilization, air drying), milling (ball mill, jet mill, wet mill), post production surface modifications (PEGylation, attachment of targeting molecules including peptides, and antibodies.

1. Hydrolysis of the initial tetra or tri methoxy (or ethoxy) silanes
   a. Nomenclature
      i. Tetra methoxy silane $(CH_3O)_4Si$
      ii. Substituted trimethoxy silane $(CH_3O)_3Si—X$, where X can be an alkyl chain, or a variably length alkyl chain with any of the following: thiol, carboxyl, amine, PEG, sugar, peptide, polysaccharide)
      iii. Same for tetra ethoxy silanes and triethoxy silanes
   b. Approach (for methoxy based silanes) Based on the Brinker method.
      i. Objective
         1. Only hydrolyze one of the four or three methoxy groups
         2. Having only one group hydrolyzed favors the formation of a liner polymeric gel formed during the condensation step. The linear polymeric structure favors slower release profiles. The condensation step allows for the formation of linear or highly branched polymeric gels structures. Starting with the single hydrolysis provides both options during the condensation reaction (see below)
      ii. Strategy
         1. Use a one to one ratio of water to Si with an excess of methanol.
         2. Low pH
         3. Hydrolyze multiple silanes separately using the appropriate established Brinker methodology (pH, temperature) and then combine when they have undergone the single methoxy hydrolysis (published protocols)
2. Condensation
   a. The structure of the resulting hydrogel depends on the relative amount of alcohol condensation versus water condensation.
   b. Conditions favoring the alcohol condensation (the free OH on the hydrolyzed silane reacts with methoxy group of another silane displacing methanol) result in linear polymers and tighter packing of the polymers in the hydrogel resulting particles with slower release profiles.
   c. Conditions favoring water condensation (a free hydroxyl from water replaces the methoxy) results in branched polymers and looser hydrogels- and loaded particles. These particles have much higher rates of release compared to the alcohol-based condensation.
   d. Temperature, pH, solvent are all factors that allow for the balance between the two extreme condensation limits. In general, the higher the pH, the more water condensation (and the faster the gelation time).
3. Loading the deliverable.
   a. The resulting hydrogel monolith is bathed in a solution containing the dissolved deliverable. The nature of the deliverable determines what solvent is most appropriate. The solvent needs to be sufficiently volatile so as to be removed during the lyophilization process. Once the hydrogel is loaded with the deliverable the material is ready of the drying step.
4. Lyophilization
   a. Upon lyophilization, the resulting material is typically a very dry powdery cake like material
5. Milling
   a. Dry milling the resulting lyophilized material yields a fine powder comprised on micron sized particles
   b. Wet milling results in particles have a diameter in the 100 nm regime
      i. The choice of solvent depends on the solubility of the deliverable
      ii. Lipophilic deliverables can be wet milled in an aqueous medium and vice versa for hydrophilic deliverables In one embodiment, disclosed is a method of preparing nanoparticle and/or microparticles loaded with a deliverable comprising the steps of:
(a) hydrolyzing with a 1:1 ratio of water (at low pH) plus methanol (4 to 10 fold excess) to Si, TMOS and any other hydrolysable silane including substituted trimethoxy silanes (where the substitution for the fourth methoxy group can be any of variety of groups including alkyl chains of varying length, alkyl chains with thiols, amines, carboxyl, carbonyl, PEG, peptides, sugars, polysaccharides)
(b) combining and mixing/sonicating the multiple hydrolyzed silanes (if multiple silanes are being used) form a uniform solution; if a single silane is being used, only the sonication step is required (c) initiating the condensation/gelation reaction by addition and fully mixing in of water at a specific pH to the hydrolyzed solution where the pH and temperature at which the mixture is maintained controls the rate and nature of the condensation process with the specific combination of hydrolyzed silanes also contributing to the rate and nature of the condensation reaction; additional options include the addition of small chain PEG (PEG 200 or 400) which also impacts the release profile of the deliverables (d) removing the resulting solid hydrogel (sol-gel) monolith after gelation/condensation is complete.

(e) adding to the partially crushed monolith a solution containing the deliverable (approximately 50 microliters of solution to 100 mg of sol-gel) and then allowing the combination to incubate;

(f) lyophilizing the resulting hydrogel to form a dry material;

(g) ball-milling or jet milling the dry material to form a powder; and if needed wet milling to form a slurry of smaller particles and (h) Optionally, the resulting particles are mixed with a solution or suspension of PEG which could include derivatized PEG to allow both for attachment to free thiols or amines on the surface of the particles and for the attachment to the PEG of: i) targeting molecules such as peptides or antibodies; and ii) imaging agents including fluorophores and other contrast agents.

Composition of the Nanoparticle Delivery Platform

Chemistry

In one embodiment, the platform is based on hydrogels forms from polymerized silanes such as tetramethoxysilane (TMOS): four methoxy groups coordinated to a Si core.

There is an initial hydrolysis phase followed by a condensation phase that results in hydrogel formation.

The hydrolysis and condensation steps can be precisely controlled (temp, water:alcohol ratio, pH) to provide different sized polymers and different degrees of polymer packing within the resulting hydrogel all of which can be exploited to control drug release profiles.

In one embodiment, the starting hydrolyzed silane can be doped with other hydrolyzed silanes that have substitutions at one of the four sites (X-trimethoxysilanes with X being a group that can be include thiols, amines, alkanes of varying size and configuration, lipids, PEG, sugars, carboxys, carbonyl, peptides, etc., etc.). In one embodiment, the condensation reaction results in the incorporation of the X-trimethoxy silane into the hydrol polymeric network. In one embodiment, the release rates of deliverables can be further tuned (beyond the control of the polymeric packing factors described above) by doping with silanes where X impacts the stability of the deliverable within the resultant nanoparticle. In certain embodiments, hydrophobicity, hydrophilicity, steric factors, charge stabilization can all be tuned.

In one embodiment, there is a slowed release of nanoparticles loaded with a dye called Evans Blue, which is a highly charged (negative) water soluble dye molecule used for imaging vascular leakage. When loaded into undoped nanoparticles, release is immediate and complete when the particles are introduced into an aqueous environment. When the hydrogel is doped with amine groups, the release rate is slowed by several orders or magnitude.

In one embodiment, the hydrolyzed silanes can also be doped with small PEG chains and/or chitosan both of which impact release rates.

In one embodiment, the hydrogel blocks are lyophilized and then machined with a ball mill to create either nanoparticles or microparticles. In one embodiment, dry ball milling yields micron sized particles. In one embodiment, wet milling after the dry milling results in nanoparticles (~150 nm diameter).

Other silane based approaches use a drip method that does not lend itself to the facile modifications and drug loading options provided by this protocol. The initial protocol entailed mixing the deliverable in with the hydrolyzed material prior to condensation. Although this approach yielded nanoparticles that had high efficacy in topical and systemic studies (as described in our numerous publications), it had limitation since the addition of the deliverable set limitations on how the hydrogel could be prepared. This aspect made it difficult to tune the properties of the resulting drug loaded nanoparticles (release rates, post production surface modifications such as PEGylation).

The presently disclosed platform technology (referred to as the ultimate drug delivery platform or UDDP) allows for the preparation of the hydrogel without the deliverable and then loading the deliverable into the empty hydrogel monolith followed by lyophilization and then machining as before.

The advantages of the UDDF approach include:

Design of the hydrogel matrix without the complication of different deliverables impacting the condensation chemistry;

Preparation of hydrogels with desired properties that require preparative conditions that would destroy many deliverables (e.g. low pH, high temperature, solvent issues);

Successfully loaded a large array of deliverables both hydrophilic and hydrophobic with great success and have been able to tune release rates;

Loading is much easier with the UDDP and much higher amounts of deliverable can be loaded. Excessive loading in the original platform was precluded due to interference (or even stoppage) of the condensation reaction and limitations on solvent. Curcumin loaded nanoparticles have been prepared using the UDDP that have six times the concentration of curcumin compared to the original curcumin loaded nanoparticles;

Options for preparing nitric oxide releasing nanoparticles.

The original platform utilized a solid state reduction of nitrite to generate nitric oxide. The nitrite was loaded into the pre-condensation mix.

Using the UDDP there are at least three strategies for generating NO releasing nanoparticles:

(i) Dope the blank hydrogel with thiols (using a thiol containing trimethoxy silane precursor). Treatment of the resulting hydrogel with stoichiometric amounts of nitrite plus low pH buffer converts the free thiols to nitrosothiols. The resulting nanoparticles manifest very slow sustained delivery of NO that we have shown to be effective in killing MRSA, vasodilation (IV infused in rodents). The amount of deliverable NO can be easily and precisely tuned. The amount of NO released is in excess of what we were releasing in the earlier platform.

(ii) The nitrite based approach has been extended to the UDDP with considerable success. We are still testing variations on the approach to create stable nanoparticle capable of a burst release of NO when exposed to water at biological temperatures (iii) Prepare nanoparticles that can slowly release nitrosothiol containing small molecules derived from glutathione, N-acetylcysteine(NAC) and other thiol containing molecules. The released nitrosothiol molecules have NO like bioactivity but are more stable and long lasting compared to free NO and have some additional properties that expand beyond the capabilities of just free NO.

For the sol-gel/hydrogel based nanoparticles of the present application, the sol-gel process is a wet-chemical technique used for the fabrication of both glassy and ceramic materials. In this process, the sol (or solution) evolves gradually towards the formation of a gel-like network containing both a liquid phase and a solid phase. The precursors undergo hydrolysis and polycondensation reactions to form a colloid. The basic structure or morphology of the solid phase can range anywhere from discrete colloidal particles to continuous chain-like polymer networks.

In certain embodiments, the sol-gel/hydrogel based nanoparticles of the present application have the ability to load a wide variety of deliverables into the interior of the nanoparticle with control over release profiles. This provides both a robust nanoparticle framework and an interior that loosen upon exposure to moisture thus allowing for slow sustained release of drugs. The nature of the preparative phase allows for easy loading of virtually any type of biological or therapeutic agent of the appropriate dimensions.

In one or more embodiments, the nanoparticle platform has the flexibility of allowing for tuning of the interior by doping the sol-gel/hydrogel using different trimethoxysilane derivatives added to the tetramethoxy or tetraethoxy silane (Tetramethyl orthosilicate [TMOS] and Tetraethyl orthosilicate [TEOS], respectively) that is used to create the hydrogel network. For example, TMOS or TEOS can be doped with trimethoxysilane derivatives that, at their fourth conjugation site (i.e., $Si(OCH_3)_3(X)$), contains derivatives such as a thiol-containing side chain, a lipid-containing side chain, a PEG-containing side chain, or an alkyl side chain of variable length. This doping allows for the introduction of side chains that can modify the over charge of the nanoparticles, tune the hydrophobicity and polarity of the interior, and introduce reactive groups that allow for chemical modifications on the surface (e.g., thiols, amines). This capability allows for control of customize loading and release properties of the nanoparticles to match the deliverable and the therapeutic application.

In one or more embodiments, the nanoparticle platform also allows for the introduction of different size PEGs into the hydrogel matrix. The size of the introduced PEG can be used to control the rate of release of the loaded drugs.

In one or more embodiments, the sol-gel/hydrogel nanoparticle platform allows for the generation and slow release of nitric oxide from within the nanoparticle. This capability allows for slow, sustained release of nitric oxide at the site of the targeted tissues.

In one or more embodiments, the sol-gel/hydrogel nanoparticles of the present application are also designed to make the resulting nanoparticles more uniform with respect to size distribution and more compact with respect to the internal polymeric network (resulting in a slower release profile). In at least one embodiment, the nanoparticle platform includes alcohol, which reduces water content (decreases the internal water content) and thus enhance the hydrogen bonding network of the nanoparticles. The use of increased fractions of alcohol in the preparation phase can result in smaller nanoparticles with a narrower distribution of sizes, and slower release profiles. Toxicity due to the use of alcohol is not an issue because of the lyophilization process, which removes all volatile liquids including free water and alcohol.

Further, in one or more embodiments, one or more amine groups can be incorporated into the polymeric network of the nanoparticle through the addition of amine-containing silanes (e.g., aminopropyltrimethoxysilane) with TMOS or TEOS for example, which accelerates the polymerization process and also contributes to a tighter internal hydrogen bonding network. The addition of amine-containing silanes can also contribute to general improvement in the suspension qualities of the nanoparticles. Moreover, the addition of amine groups can help in the attachment of PEGs, peptides, and other amine-binding molecules on the surface of the nanoparticles as a means of extending systemic circulation time and increasing the probability of localization at a target site with leaky vasculature. The net effect of these additions are nanoparticles that release drugs and additives more slowly and more uniform in size distribution. Further, these modifications improve the suspension properties of the nanoparticles (e.g., minimize aggregation), allow for tuning of the average size of the nanoparticles, and allow for delivery of nitro fatty acids and highly lipophilic molecules.

In at least one aspect, the present application provides for a method of enhancing the delivery of therapeutic agents, imaging agents, and theranostics in nanoparticles via the use of fatty acids. In one or more embodiments, the method comprises incorporating fatty acids such as myristic acid, oleic acid, and other conjugated fatty acids (e.g., linoleic acid, conjugated linoleic acid) individually or in combination into the platform for hybrid-hydrogel based nanoparticles. When these are included in the nanoparticle, the resulting nanoparticles can contain nitro fatty acids, which are highly anti-inflammatory and potentially chemotherapeutic. Alternatively, nitro fatty acids can be prepared and then incorporated into the recipe for generating the nanoparticles. The introduction of oleic acid or conjugated linoleic acid, and/or other unsaturated fatty acids into the nanoparticle also provides a lipophilic interior to the nanoparticles that will enhance loading of lipophilic deliverables. The incorporation of one or more fatty acids into the nanoparticle platform can enhance skin penetration, sublingual and suppository-based (e.g., rectal, vaginal) delivery, and systemic delivery via uptake from the gut subsequent to oral ingestion. Specifically, the incorporation of myristic acid into the nanoparticle platform can facilitate improvements in cardiovascular endpoints (e.g., blood pressure, heart rate), and erectile dysfunction. In an alternative embodiment, the one or more fatty acids can be applied to the coatings of gadolinium oxide-based paramagnetic nanoparticles as a means of facilitating systemic delivery via oral, sublingual, or suppository routes.

Another modification to the hybrid-hydrogel nanoparticles include doping the TMOS or TEOS with trimethoxy silane derivates that at their fourth conjugation site (e.g., $Si(OCH_3)_3(X)$) contains derivatives such as a thiol-containing side chain, a lipid-containing side chain, a PEG-containing side chain, or an alkyl side chain of variable length. Other additives can also be added to the nanoparticles to enhance its physical properties, such as polyvinyl alcohols.

Composition Comprising Modified Nanoparticles

In certain embodiments, the modified nanoparticles of the present application can be incorporated into one or more compositions. These compositions can contain a therapeutically effective amount of a modified nanoparticle, optionally more than one modified nanoparticle, preferably in purified form, together with a suitable amount of a pharmaceutically acceptable vehicle so as to provide the form for proper administration to the patient. In certain embodiments, the composition contains 1-5%, 5-10%, 10-20%, 20-30%, 30-40% modified nanoparticle.

In certain embodiments, the modified nanoparticles are administered to a subject using a therapeutically effective regimen or protocol. In certain embodiments, the modified nanoparticles are also prophylactic agents. In certain embodiments, the modified nanoparticles are administered to a subject or patient using a prophylactically effective regimen or protocol.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. In certain embodiments, an elderly human, human adult, human child, human infant. The term "vehicle" refers to a diluent, adjuvant, excipient, or carrier with which a compound of the present application is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the modified nanoparticles and pharmaceutically acceptable vehicles are preferably sterile. Water is a preferred vehicle when the modified nanoparticle is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions comprising the modified nanoparticles, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical vehicles are described in "Remington's Pharmaceutical Sciences" by E. W. Martin.

In a preferred embodiment, the compounds of the present application are formulated in accordance with routine procedures as a pharmaceutical composition adapted for intravenous administration to human beings. Typically, compounds of the present application for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the present application is to be administered by infusion, it can be dispensed, for example, with an infusion bottle containing sterile pharmaceutical grade water or saline. Where the modified PMNP is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the present application. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

Types of Disease and Disorders

The present disclosure provides methods of treating or preventing or managing a disease or disorder in humans by administering to humans in need of such treatment or prevention a pharmaceutical composition comprising an amount of modified nanoparticles effective to treat or prevent the disease or disorder. In other embodiments, the disease or disorder is an inflammatory disease or disorder.

The present application encompasses methods for preventing, treating, managing, and/or ameliorating an inflammatory disorder or one or more symptoms thereof as an alternative to other conventional therapies. In specific embodiments, the patient being managed or treated in accordance with the methods of the present application is refractory to other therapies or is susceptible to adverse reactions from such therapies. The patient may be a person with a suppressed immune system (e.g., post-operative patients, chemotherapy patients, and patients with immunodeficiency disease, patients with broncho-pulmonary dysplasia, patients with congenital heart disease, patients with cystic fibrosis, patients with acquired or congenital heart disease, and patients suffering from an infection), a person with impaired renal or liver function, the elderly, children, infants, infants born prematurely, persons with neuropsychiatric disorders or those who take psychotropic drugs, persons with histories of seizures, or persons on medication that would negatively interact with conventional agents used to prevent, manage, treat, or ameliorate a viral respiratory infection or one or more symptoms thereof.

In certain embodiments, the present application provides a method of preventing, treating, managing, and/or ameliorating an autoimmune disorder or one or more symptoms thereof, said method comprising administering to a subject in need thereof a dose of an effective amount of one or more pharmaceutical compositions of the present application. In autoimmune disorders, the immune system triggers an immune response and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress, destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin.

Examples of autoimmune disorders that can be prevented, treated, managed, and/or ameliorated by the methods of the present application include, but are not limited to, adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, dense deposit disease, discoid lupus, essential mixed cryoglobulinemia, fibromyalgia-fibromyositis, glomerulonephritis (e.g., IgA nephrophathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, lichen planus, lupus erythematosus, Meniere's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychrondritis, Polyendocrinopathies, polyglandular syndromes, polymyalgia rheumatica, polymyositis and dermatomyositis, post-MI, primary agammaglobulinemia, primary biliary cirrhosis, psoriasis, psoriatic arthritis, Raynauld's phenomenon, relapsing polychondritis, Reiter's syndrome, rheumatic heart disease, rheumatoid arthritis, sarcoidosis, scleroderma, Sjogren's syndrome, stiff-man syndrome, systemic lupus erythematosus, takayasu arteritis, temporal arteritis/giant cell arteritis, ulcerative colitis, urticaria, uveitis, Uveitis Opthalmia, vasculitides such as dermatitis herpetiformis vasculitis, vitiligo, and Wegener's granulomatosis.

Mode of Administration

The present compositions, which comprise one or more modified nanoparticles, can be administered by infusion or bolus injection, by absorption through epithelial or mucocutaneous linings (e.g., oral mucosa, rectal and intestinal mucosa, etc.) or orally and may be administered together with another biologically active agent. Administration can be systemic or local. Various delivery systems are known. In certain embodiments, more than one modified nanoparticle is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the modified nanoparticle into the bloodstream.

In specific embodiments, it may be desirable to administer one or more compounds of the present application locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site).

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the present application can be formulated as a suppository, with traditional binders and vehicles such as triglycerides.

In yet another embodiment, the compounds of the present application can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target of the modified nanoparticle, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

Dosage

The amount of a modified nanoparticle that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the present application per kilogram body weight. In specific preferred embodiments of the present application, the oral dose is 0.01 milligram to 70 milligrams per kilogram body weight, more preferably 0.1 milligram to 50 milligrams per kilogram body weight, more preferably 0.5 milligram to 20 milligrams per kilogram body weight, and yet more preferably 1 milligram to 10 milligrams per kilogram body weight. In another embodiment, the oral dose is 5 milligrams of modified nanoparticle per kilogram body weight. The dosage amounts described herein refer to total amounts administered; that is, if more than one modified nanoparticle is administered, the preferred dosages correspond to the total amount of the modified nanoparticles administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of modified nanoparticles per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the modified nanoparticles for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The present application also provides pharmaceutical packs or kits comprising one or more containers filled with one or more modified nanoparticles. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one modified nanoparticle. In another embodiment, the kit comprises a modified nanoparticle and a second therapeutic agent.

The modified nanoparticles are preferably assayed in vitro and in vivo, for the desired therapeutic or prophylactic activity, prior to use in humans. For example, in vitro assays can be used to determine whether administration of a specific modified nanoparticle or a combination of modified nanoparticles is preferred for lowering fatty acid synthesis. The modified nanoparticles may also be demonstrated to be effective and safe using animal model systems.

Other methods will be known to the skilled artisan and are within the scope of the present application.

Combination Therapy

In certain embodiments, the modified nanoparticles of the present application can be used in combination therapy with at least one other therapeutic agent. The modified nanoparticles and the therapeutic agent can act additively or, more preferably, synergistically. In a preferred embodiment, a composition comprising a modified nanoparticle is administered concurrently with the administration of another therapeutic agent, which can be part of the same composition as the modified nanoparticle or a different composition. In another embodiment, a composition comprising a modified nanoparticle is administered prior or subsequent to administration of another therapeutic agent. As many of the disorders for which the modified nanoparticles are useful in treating are chronic disorders, in one embodiment combination therapy involves alternating between administering a composition comprising a modified nanoparticle and a composition comprising another therapeutic agent, e.g., to minimize the toxicity associated with a particular drug. The duration of administration of each drug or therapeutic agent can be, e.g., one month, three months, six months, or a year. In certain embodiments, when a modified nanoparticle is administered concurrently with another therapeutic agent that potentially produces adverse side effects including but not limited to toxicity, the therapeutic agent can advantageously be administered at a dose that falls below the threshold at which the adverse side is elicited.

Any therapy (e.g., therapeutic or prophylactic agent) which is useful, has been used, or is currently being used for the prevention, treatment, and/or management of a disorder, can be used in compositions and methods of the present application. Therapies (e.g., therapeutic or prophylactic agents) include, but are not limited to, peptides, polypeptides, conjugates, nucleic acid molecules, small molecules, mimetic agents, synthetic drugs, inorganic molecules, and organic molecules. In certain embodiments, a prophylactically and/or therapeutically effective regimen of the present application comprises the administration of a combination of therapies.

In a preferred embodiment, the invention provides a method of preparing a nanoparticle and/or microparticle loaded with a drug comprising the steps of:
(a) hydrolyzing a silane, tetramethoxy silane (TMOS), or a hydrolysable silane using methanol and water having a pH≤3 to form a mixture;
(b) combining water having a pH between 5-8, optionally polyethylene glycol (PEG), and optionally a drug, with the mixture of step (a) to form a solid hydrogel monolith, which optionally comprises PEG and/or a drug;
(c) removing the resulting solid hydrogel monolith;
(d) optionally incubating the monolith with a drug to form a hydrogel drug composition, wherein the drug is step (d) can be the same or different than the drug in step (b);
(e) lyophilizing the composition of step (d) to form a dry material;
(f) ball-milling or jet milling the dry material of step (e) to form a powder; or alternatively wet milling forming a slurry of particles; and
(g) optionally applying to the surface of the particles after wet milling one of more of a polyethylene glycol (PEG), an anion, a cation, or an alkane;
thereby preparing a nanoparticle and/or microparticle loaded with one or more drugs.

Preferably, the water added in step (a) has a pH of about 1.4. Preferably, in step (a) the methanol is present in a concentration of 25% to 75%. More preferably, the methanol is present in a concentration of about 45%. Preferably, step (a) is carried out at a temperature of about 60° C. for about 1.5 hours.

Fabrication of the hydrogel monolith is a two-step process, where step (a) is hydrolysis, and step (b) is condensation. Both steps are dependent on pH and solvent composition. In step (a) the apparent pH is below 3. In step (b) the apparent pH is in the range of 5-8. Furthermore, there is additional water added in step (b). Both higher pH and additional water promote the condensation reaction.

Preferably, the hydrolysable silane comprises a substituted trimethoxy silane, wherein the trimethoxy silane is substituted with one or more of an alkyl chain, an alkyl chain with a thiol, an amine, carboxyl, carbonyl, PEG, peptide, sugar, or polysaccharide, or a combination thereof.

Preferably, the PEG is a PEG200 daltons to PEG10K daltons. Often, the PEG is PEG200 daltons to PEG400 daltons. PEG is frequently added to step (b) of the process. This alters the pore and release characteristics. Alternatively, or in addition, the surface of the particles can be PEGylated. Surface PEGylation alters the interfacial properties; i.e. how the particles interact with each other and with cells and tissues; especially in circulation, it will prevent particles from occluding in the veins. Also, PEGylation renders the particles undetectable by macrophage and other immune cells. In different embodiments, a targeting molecule comprising a peptide, antibody, imaging agent or a combination thereof is attached to the PEG.

Examples of anions that can be applied to the surface of the particles include methylphosphonate. Examples of cations that can be applied to the surface of the particles include amines. Examples of alkanes that can be applied to the surface of the particles include octyl groups. Treatment of the particles with anions or cations can make the particles dispersable.

The invention also provides a nanoparticle and/or microparticle loaded with one or more drugs prepared by any of the methods disclosed herein. The invention further provides a method of treating a subject with a disease or disorder comprising administering to the subject a therapeutically effective amount of any of the nanoparticles and/or microparticles disclosed herein.

Differences from Related Technologies

The present invention provides advantages over previous technologies. Other technologies and how the present ultimate drug delivery platform (UDDP) differ are described below.

Stober Process-Based Production of Silane Derived Nanoparticles:

Nanoparticles are generated through a solution/solvent phase process that is highly sensitive to the reactants. In contrast, simple and robust Brinker type chemistry is used for the UDDP without the complex manufacturing and chemical (e.g., ammonia) requirements needed for the Stober process. Physical properties are easily tuned for the UDDP by manipulating the Brinker process derived empty monolith sol-gel through well-established simple steps such as through pH and temperature changes. It is not obvious how that flexibility can be achieved (if at all) using the Stober process.

The Stober process requires complex reaction conditions and numerous reagents (e.g., ammonia) which are not needed for the UDDP.

The Stober process has very limited loading capabilities for deliverables in contrast to the UDDP where there is facile loading of any moderate to small sized molecule including both hydrophilic and lipophilic molecules. The Stober process would require the loading of the deliverable through physico-chemical forces occurring during the process of particle formation. Given the complexity of the Stober process it is not clear that it is even possible to create the conditions to load most of the deliverables that are easily loaded into the UDDP derived particles. It is also likely that each deliverable would require a unique set of synthesis conditions for the Stober process derived particles. The UDDP process utilizes loading of the deliverables into sol-gel after the hydrolysis and condensation phases for gel formation are complete hence there is no interference of the deliverable with the sol-gel chemistry. All subsequent steps are non-chemical. Thus, the UDDP methods allows a separation of the gel preparation phase from the loading phase which provides tremendous flexibility with respect to manipulating the physical properties of the internal and external features of the resulting particles independent of the deliverable.

NO releasing nanoparticles have also been generated through the more complex Stober process (Schoenfish patent and papers) by doping with thiol containing silanes ad then generating S-nitrosothiols, but there is very limited capability for manipulation of physical properties of the particles and for the inclusion of other deliverables. Similar NO releasing particles are easily prepared using the UDDP but with all the added potential modifications that can be derived from the UDDP.

Silica Particles:

Silica based nanoparticles can be loaded with certain deliverables by passively loading the particles, but there are significant limitations with respect to amount of loading, what can be loaded and control of release rates.

In contrast for the UDDP, loading the silane-derived hydrogel monoliths after gelation but prior to particle formation allows for easy manipulation of the physical properties including release profiles for the to be loaded deliverables, prior to loading. The UDDP derived gels can easily be modified to accommodate different categories of deliverables. This flexibility is not evident for synthetic strategies that utilize silica particles.

Hybrid Hydrogel Platform:

The composition of the UDDP particles and the hybrid hydrogel particles have some overlap, but there are clear differences in the two processes. The primary difference is that for the earlier hybrid hydrogel platform, the deliverable was loaded in the initial phase of the hydrogel preparation—after hydrolysis but before condensation. As a result, the conditions for gel formation had to be manipulated to accommodate the added deliverable, which placed major limitations on the sol-gel preparative phase. Many deliverables when added undermined the chemistry for gelation preventing the formation of loaded sol-gel monoliths. Conditions for gelation had to be sufficiently gentle and rapid to avoid damage to the deliverable or to avoid possible unwanted reactions. The amount of the deliverable for molecules that were compatible with gel formation was limited by the amount that could be added without undermining the gelation. Thus, for the UDDP particles at least a six-fold enhancement of curcumin loading per mg of resulting particle could be achieved by using a solvent that for curcumin had a higher solubility compared to the solvents that were required for the successful gelation for the hybrid hydrogel platforms. This limitation was also very apparent when trying to load oils, lipids etc. into the hybrid hydrogel particles. Very low concentrations of these deliverables were necessary in order to create conditions for gelation. In contrast for the UDDP, fully formed sol-gel monoliths can be loaded with much higher amounts of these deliverables.

Release rates. The earlier hybrid platform, as well as all other competing technologies, do not allow for facile manipulation of release rates. The hybrid platform allowed for some manipulation by incorporating different sized PEG chains into the particles. This technique was very limited. In contrast the UDDP process allows for the manipulation of the interior of the nanoparticle independent of what is loaded. Thus, well-known straight forward strategies for creating different internal structures within the initial hydrogel block using Brinker chemistry/physics allows for tight and loose internal structures that translate into different release profiles. Additionally, the initial mix for generating the hydrogel can be doped with organosilanes having a variety of side chains thus allowing for tuning the internal environment with respect to lipophilicity, charge, water content, hydrogen bonding capabilities, reactive groups that can covalently bind contrast agent as well as a nitric oxide, peptides, and many other reactive agents.

The UDDP is not an Obvious Extension of any of these Previous Technologies.

It was never obvious that the sol-gel monoliths could be loaded with deliverables after formation and it was certainly not obvious that the vast array of potential deliverables could be loaded.

It was not obvious that manipulation of the gelation process using simple variations in solvent composition, pH and temperature could be so effective at controlling release profiles.

It was not obvious that one could achieve modulating of release profiles from UDDP derived particles through:
  the inclusion of small PEG chains,
  covalent introduction of side chains (e.g., amines, thiols, alkyl groups of different sizes)
  modification of the polymeric network within the hydrogel; pore size is controlled by strict control of water content and pH in the two steps of the process.

EXAMPLES

The following examples refers to the preparation and characterization of Sol-gel/hydrogel nanoparticles in accordance with one or more embodiments of the present application.

| Slow release curcumin: | | | | |
|---|---|---|---|---|
| Sol-gel: | | | | |
| TMOS | 3 | mL | 1) | Combine and hold in sealed tube 1.5 hrs at 60 C. |
| MeOH | 2.465 | mL | | |
| 40 mM HCl | 0.366 | mL | | |
| 6.25 mM NaOH | 1.152 | mL | 2) | Add NaOH and PEG, hold in sealed tube at 40 C. |
| PEG 400 | 0.375 | mL | | firm gel will form in ~36 hrs |
| Wet gel (approximate) | 6.5 | g | | |
| Loading: | | | | |
| Wet gel | 6.50 | g | 1) | Pulverize gel |
| 20 mM curcumin/EtOH | 3.25 | mL | 2) | Mix in curcumin; hold for 30 mins. Freeze |
| Post lyophilization: | | | | |
| Dry gel | 1.658 | g | | |
| curcumin | 0.024 | g | | |
| Curcumin load (% weight) | 1.45% | | | |

There is a separation of the initial hydrolysis step and the subsequent condensation step (with higher pH due to the added hydroxide).

| NO releasing particles: | | | | | |
|---|---|---|---|---|---|
| mpts | 0.6 | mL | Part 1: | 1) | Combine mpts, water, 0.1M HCl, and MeOH in a tube and hold at 22 C. for 1.5 hours. |
| water | 0.974 | mL | | | (Can be held on icefor several hours) |
| 0.1M HCl | 0.226 | mL | | 2) | Add sodium nitrite; mix thoroughly to dissolve |
| MeOH | 4.8 | mL | | 3) | Add 12M HCl and mix. Solution will be cherry red. Hold mixture on ice. |
| sodium nitrite | 223 | mg | | | |
| 12M HCl | 0.267 | mL | | | |
| TMOS | 1.5 | mL | Part 2: | 4) | Combine TMOS and 1 mM HCl. Sonicate in ice water for 15 minutes or until monophasic. |
| 1 mM HCl | 0.3 | mL | | | |
| 100 mM phosphate, pH = 7.4 | 12 | mL | Part 3: | 5) | Combine phosphate buffer and PEG in a tube. |
| PEG 400 | 0.75 | mL | | | |
| Wet gel (approx) | 22 | g | | | |
| Lyophilized powder | 2.257 | g | | | |
| | | | Assembly: | | Combine part 1 (mpts solution) and part 3 (buffer/PEG) and vortex well. |
| | | | | | Add part 2 (hydrolyzed TMOS) and vortex well. |
| Results: | | | | | Hold mixture at room temperature for 30-60 minutes. |
| umoles thiol/mg powder | 1.43 | | | | Lyophilize. |
| umoles released NO/mg | 0.45 | | | | Store protected from light at −20 C. (or −80 C.). |
| Efficiency (max. to date) | 31.5% | | | | Mill or pestle powder as needed. |

The loading step for SNO nanoparticle consists of loading nitrite to the gel followed by addition of acid.

Lyophilization:

Note that the gel comprising curcumin has low water/methanol content and thus lyophilizes quickly (on the order of several hours), whereas the SNO gel will take 1-2 days to lyophilize.

Post-Lyophilization Processing:

Planetary ball mill "Fritsch Pulverisette 6"; maximum speed=650 rpm.

12 mL silicon nitride bowl or 80 mL zirconium oxide bowl

Grinding balls range from diameter=0.5 mm-10 mm.

Dry milling yields powder with average diameter=8 μm.

High speed wet milling (in water, propylene glycol, or alcohol, etc.) yields nanoparticle suspension as small as diameter=150 nm, dependent on grinding balls, milling speed, and milling duration.

A significant degree of particle size reduction can be quickly achieved for small samples with agate mortar and pestle (wet or dry).

Nitric Oxide Detection:

Sievers 280i Nitric Oxide Analyzer 5 mg powder dispersed in 5 mL buffer, pH 7.4

Vessel is bubbled with high purity nitrogen (200 mL/minute) that carries released NO to ozone-chemiluminescence based detector.

Base

Base formula (Br1):

| | | |
|---|---|---|
| TMOS | 3 mL | 1) 1.5 hrs at 60 C. |
| MeOH | 2.465 mL | |
| 40 mM HCl | 0.366 mL | |
| Water | 1.152 mL | 2) Add water, 3 days at 40 C. |

Composition Adjusted pH (NaOH):

| | | |
|---|---|---|
| TMOS | 3 mL | 1) 1.5 hrs at 60 C. |
| MeOH | 2.465 mL | |
| 40 mM HCl | 0.366 mL | |
| NaOH | 1.152 mL | 2) Add NaOH solution, hold at 40 C. |
| → 6.25 mM | | apparent pH 2.9; forms gel in 36 hours |
| → 9.38 mM | | apparent pH 3.2; forms gel in 2 hours |
| | | apparent pH 4.4; forms gel in 20 minutes |
| → 12.5 mM | | |

PEG dispersed:

| | | |
|---|---|---|
| TMOS | 3 mL | 1) 1.5 hrs at 60 C. |
| MeOH | 2.465 mL | |
| 40 mM HCl | 0.366 mL | |
| Water | 1.152 mL | 2) Add water and PEG, hold at 40 C. |
| PEG 400 | | |
| → low | 0.375 mL | firm gel in 7 days |
| → med | 0.750 mL | firm gel in 8 days |
| high | 1.5 mL | firm gel in 10 days |

Trimethoxy doped (3%):

| | | |
|---|---|---|
| TMOS | 3 mL | 1) 1.5 hrs at 60 C. |
| Dopant | | |
| → MPTS | 0.113 mL | |
| → IBTS | 0.117 mL | |
| → OTS | 0.158 mL | |
| → VTS | 0.093 mL | |
| → ODTS | 0.258 mL | |
| → MTS | 0.087 mL | |
| → MeOH | 2.465 mL | |
| 40 mM HCl | 0.366 mL | |
| Water | 1.152 mL | 2) Hold at 40 C.; firm gel |

Specialty MPTS doped/NaOH (Br SNO):

| | | |
|---|---|---|
| TMOS | 2.7 mL | 1) 1.5 hrs at 60 C. |
| MPTS | 0.3 mL | |
| MeOH | 2.465 mL | |
| 40 mM HCl | 0.366 mL | |
| 9.38 mM NaOH | 1.152 mL | 2) Add NaOH solution, hold at 40 C. for 2 hours |
| 2 M Sodium nitrite | 0.815 mL | 3) Add Sodium nitrite solution to broken gel |
| 12 N HCl | 0.134 mL | 4) Add HCl solution and mix; gel will turn red |

Chitosan, pH 5/ PEG (Br2):

| | | |
|---|---|---|
| TMOS | 3 mL | 1) 1.5 hrs at 60 C. |
| MeOH | 2.465 mL | |
| 40 mM HCl | 0.366 mL | |
| Chitosan, 0.5% pH 5 | 1.152 mL | 2) Add chitosan solution and PEG, 15 mins at 40 C. |
| PEG 400 | 1.500 mL | | pre-hydrolyzed MPTS doped:

| | | |
|---|---|---|
| TMOS | 3 mL | 1) 1.5 hrs at 60 C. |
| hydrolyzed MPTS | | |
| → 1% | 0.038 mL | |
| → 3% | 0.113 mL | |
| → 9% | 0.340 mL | |
| MeOH | 2.465 mL | |
| 40 mM HCl | 0.366 mL | |
| Water | 1.152 mL | 2) Add water, hold at 40 C. |
| | | → 1%, firm gel in 7 days |
| hydrolyzed MPTS | | → 3%, firm gel in 9 days |
| mpts | 0.6 mL | → 9%, |
| water | 0.974 mL | |
| 0.1M HCl | 0.226 mL | |
| MeOH | 4.8 mL | |

UDDP Accommodates Loading of a Wide Variety of Deliverables (FIG. 1)

FIG. 1 shows release rates for assorted deliverables. This result shows that one can load a range of lipophilic materials into the formed gels (using Br 1 protocol). Fluorescent labeled cholesterol and palmytic acid were used to show both loading and release. Procyanidine is a potent antioxidant that is being evaluated for use in the treatment of osteoarthritis.

Figure 2:
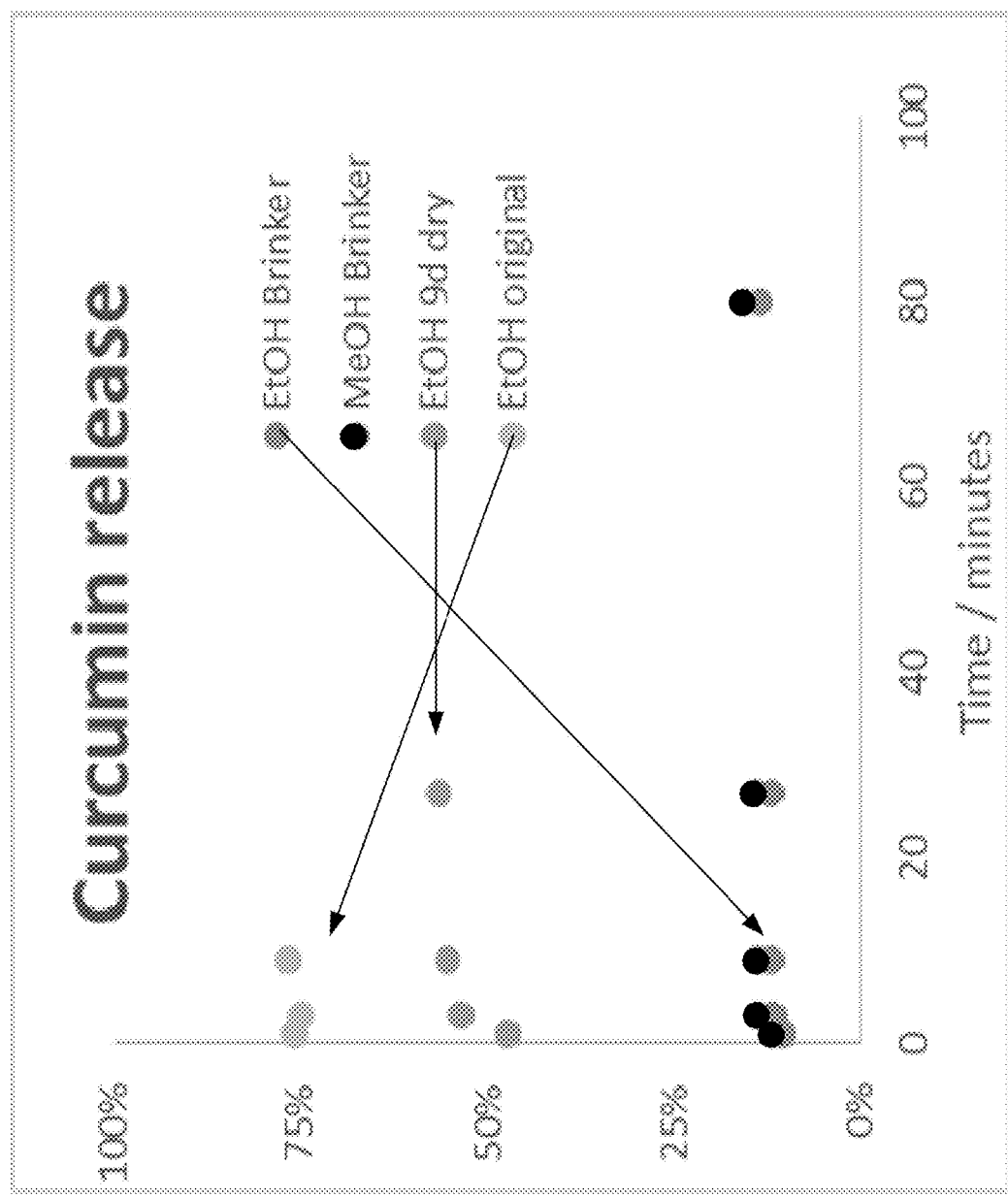
FIG. 2. A comparison of release profiles form curcumin loaded nanoparticles. "Brinker" (Br) is the high-density sol-gel that took 7 days to gel and curcumin added after the gelation is complete. "9d dry" is the original formulation air dried for 9 days. Release is of suspended particles into ethanol or methanol. Plots from top to bottom, respectively: EtOH original, EtOH 9d dry, MeOH Brinker, and EtOH Brinker.

Comparison of the Release Profiles from Curcumin Loaded Nanoparticles (FIG. 2)

Release from Nanoparticles was Made Via:
the Br(Brinker) method where the curcumin is loaded into the empty Br sol-gel block (slow gelation protocol), The original hydrogel platform where the curcumin is mixed in the initial pre-condensation mixture which gels much more rapidly than the Br sol-gels, Curcumin loaded in the original fast gelling platform but the resulting curcumin containing sol-gel is air dried for nine days (to promote enhanced density-decreasing pore size.

The results show that the curcumin particles derived from the slow gelling Br protocol show a dramatic slow down in release compared to the original platform and the air dried version of the original platform.

Figure 3A:
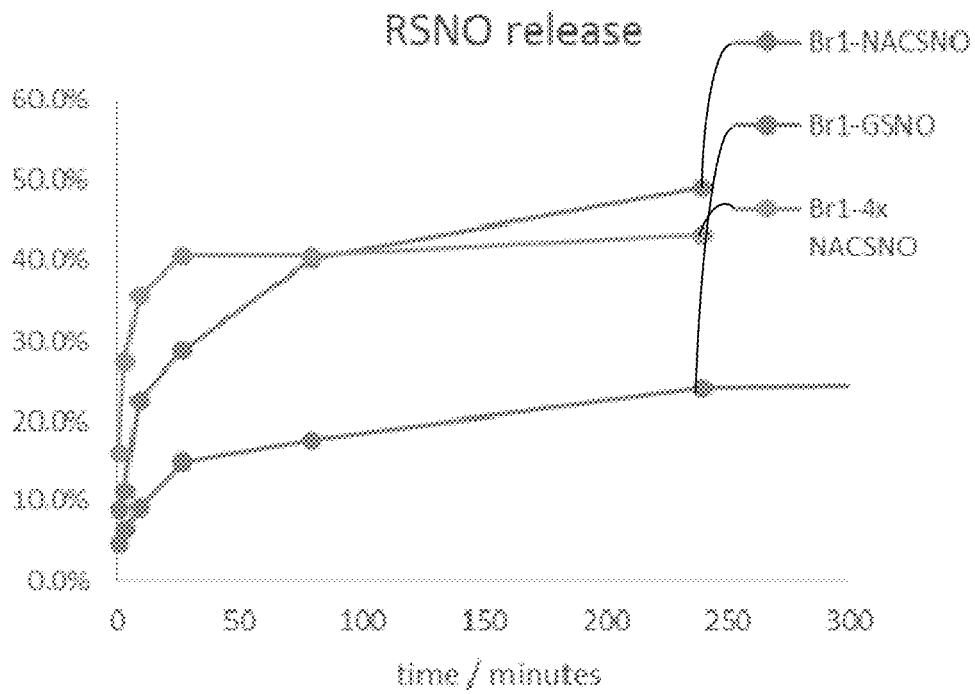
FIGS. 3A-3B. Release of GSNO and NACSNO from Br derived particles. Different time scales in (A) and (B). Plots from top to bottom, respectively, at right side of plots: Br1-NACSNO, Br1-4x-NACSNO, and Br1-GSNO.
Figure 3B:
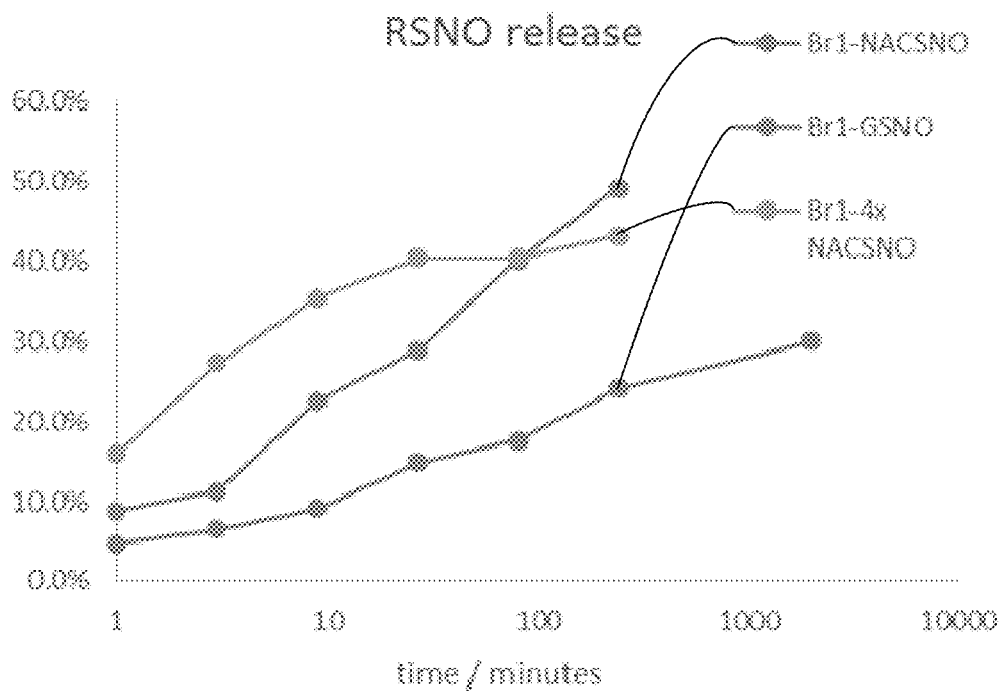

Release of GSNO and NACSNO from Br Derived Particles (FIG. 3A-3B)

The NACSNO loading into the original rapid gelation platform (NACSNO added before condensation) yield particles that exhibit almost immediate release of the NACSNO upon addition to an aqueous buffer. GSNO prepared in a similar manner was unstable and also exhibited rapid release. Loading the deliverables after preparing a Br slow gellation sol-gel block results in particles that exhibit much slower release than for the original platform. Increasing the concentration (×4) resulted in an increase in the release profile. NAC and GSH are first loaded into the Br sol-gel and then exposed to sodium nitrite in a low pH buffer to create NACSNO and GSNO without any residual nitrite.

Slow release of S-nitrosothiol containing molecules is achievable using the UDDP. The empty sol-gel monoliths are loaded with the thiol containing molecule: NAC, GSH, Captopril, N acetyl penicillamine. The addition of a nitrite followed by acid converts the thiols to S-nitrosothiols.

Lyophilization followed by milling yield the particles. The slow release requires the Br1 type preparation (low pH, very slow gelation) of the hydrogel which creates very tight packing of the polymer. Generating a looser polymeric network allows for rapid release. Gels made at high pH under rapid gelation conditions result in particles showing almost immediate and complete release of SNO containing molecules.

Additional deliverables loaded into UDDP: S-nitrosothiols (NACSNO, GSNO, SNAP), siRNA, Peptides, Evans Blue, Nitrite, Amino acids, tryptophan.

The UDDP can be Used to Generate Nitric Oxide Releasing Nanoparticles: SNO-np

The initial sol-gel block is doped with thiols that are introduced by mixing hydrolyzed TMOS with hydrolyzed X-trimethoxy silane where X is a thiol containing alkyl group bound to the Si. The mixture undergoes the condensation reaction which generates the sol-gel made with polymers that have the thiols covalently attached.

The thiols in the sol-gel monolith are converted to nitrosothiols through the addition into the sol-gel monolith of stoichiometric amounts of nitrite in buffered aqueous solution. This step is followed by the addition of a small aliquot of acid which converts nitrite to NO which then reacts with the thiols to make covalently attached nitrosothiols (SNO). The sol-gel turns pink when this reaction occurs. The resulting pink sol-gel is then lyophilized and milled to produce nano or micro particles. The NO releases in aqueous environments but release can be accelerated with light, heat, metal ions, pH.

Figure 4:
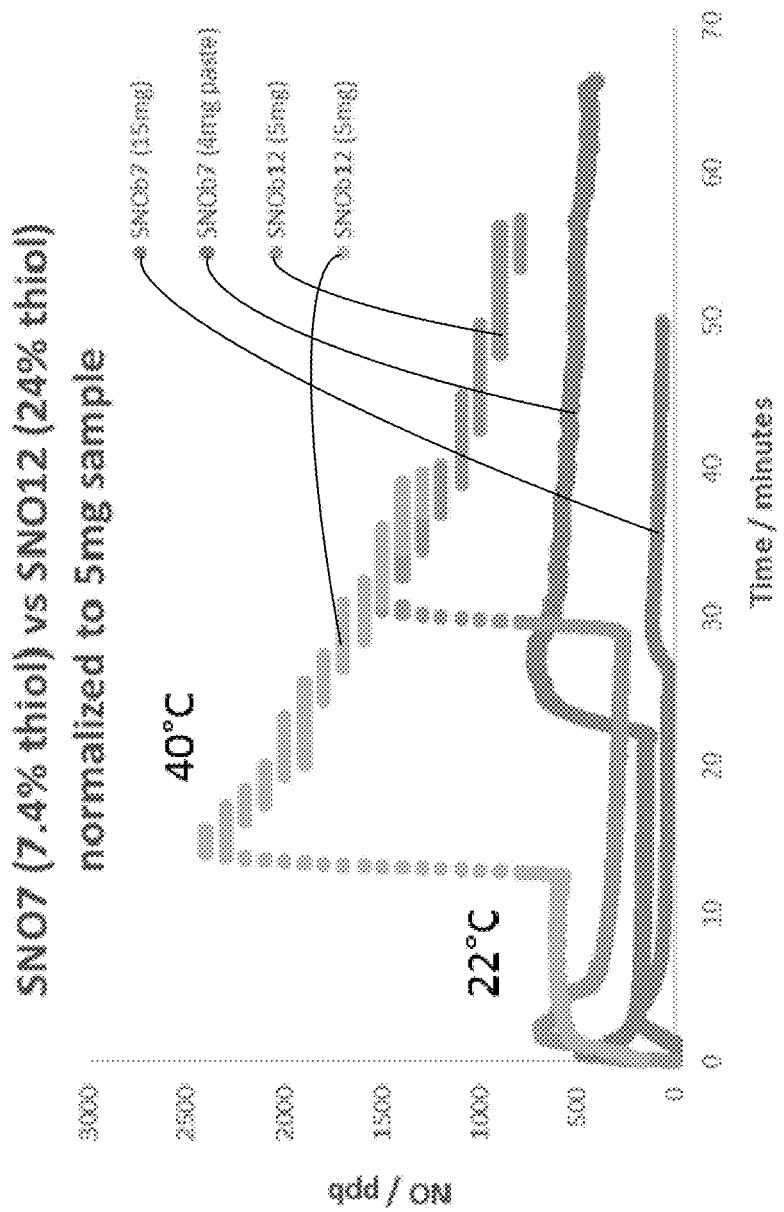
FIG. 4. NO release decreases with decreased thiol concentration. Plots from top to bottom, respectively, at right side of plots: SNOb12 (5 mg), SNOb12 (5 mg), SNOb7 (4 mg paste), and SNOb7 (15 mg).

NO Release Decreases with Decreased Thiol Concentration (FIG. 4)

NO release rate is dependent on temperature as illustrated in FIG. 4.

Figure 5:
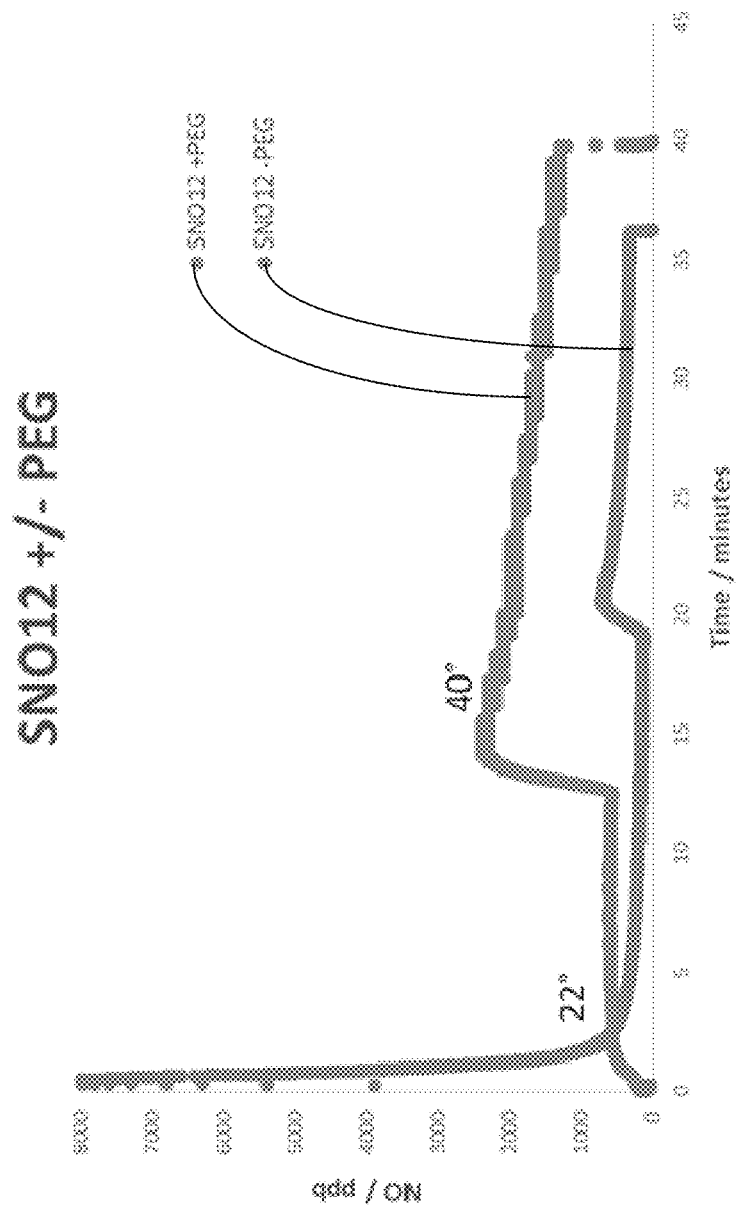
FIG. 5. Incorporation of small PEG chains into the sol-gel matrix impacts the NO loading and release for SNO-np. Plots from top to bottom, respectively, at right side of plots: SNO12+PEG and SNO12-PEG.

Incorporation of Small PEG Chains into the Sol-Gel Matrix Impacts the NO Loading and Release for SNO-np FIG. 5 illustrates an example where omission of PEG leads to a reduction in NO release. The rate of release is dependent on temperature.

Figure 6:
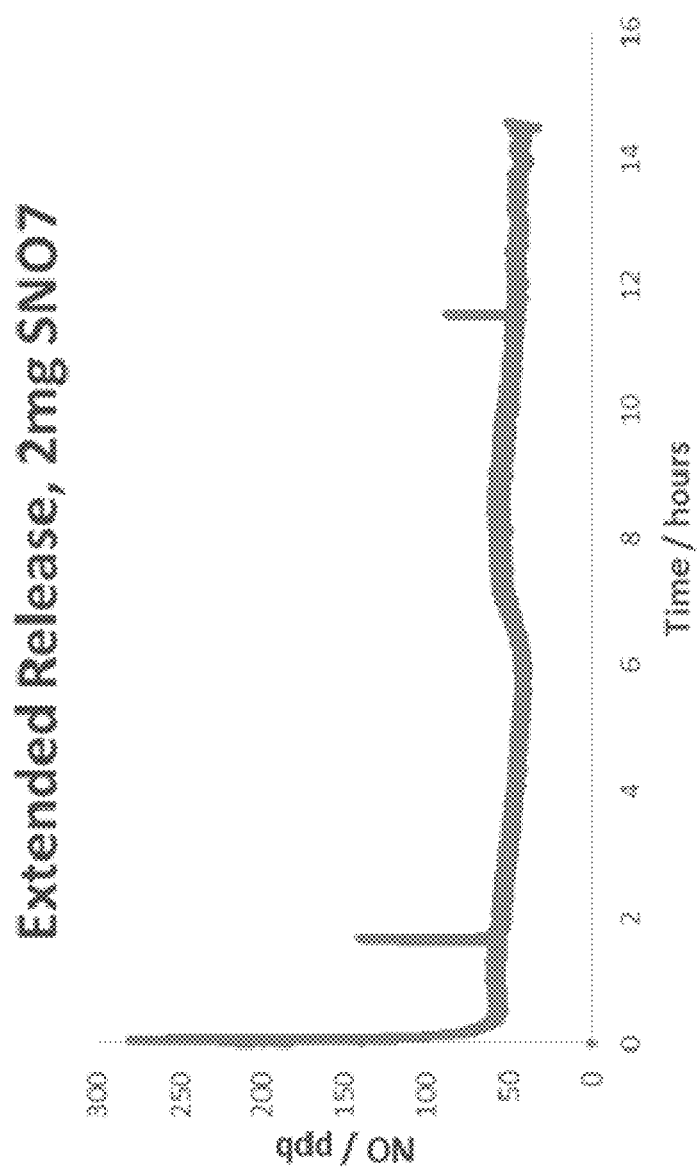
FIG. 6. Particles release steady amount of NO for over 14 hours.

The particles release steady amount of NO for over 14 hours (FIG. 6).

TABLE 1

Thiol content and SNO loading efficiency.

| Formula: | mpts/(mpts + tmos) | μmole thiol/mg | Efficiency | μmole NO/mg |
|---|---|---|---|---|
| SNO7 | 0.074 | 0.449 | 50% | 0.225 |
| SNO12 | 0.241 | 1.431 | 28% | 0.401 |
| SNO12 -PEG | 0.241 | 2.29 | 5% | 0.115 |

Facile Surface PEGylation and Fluorescent/Radioactive Labeling of Br Particles

Doping Br sol-gels with thiol (or amine) containing silanes (e.g. MPTS or APTS) allows for:
  Attachment of PEG chains on the surface of the particles;
  Covalent attachment of reactive fluorophores/contrast agents, radioactive labels (that bind to amines or thiols) within the particles (addition of reagent into the doped gels prior to lyophilization) or on the particles (addition after the particles are prepared);
  Can prepare particles that have multiple colors: one for the particles themselves and on for the PEG chain attached to the surface of the particles.

Figure 7:
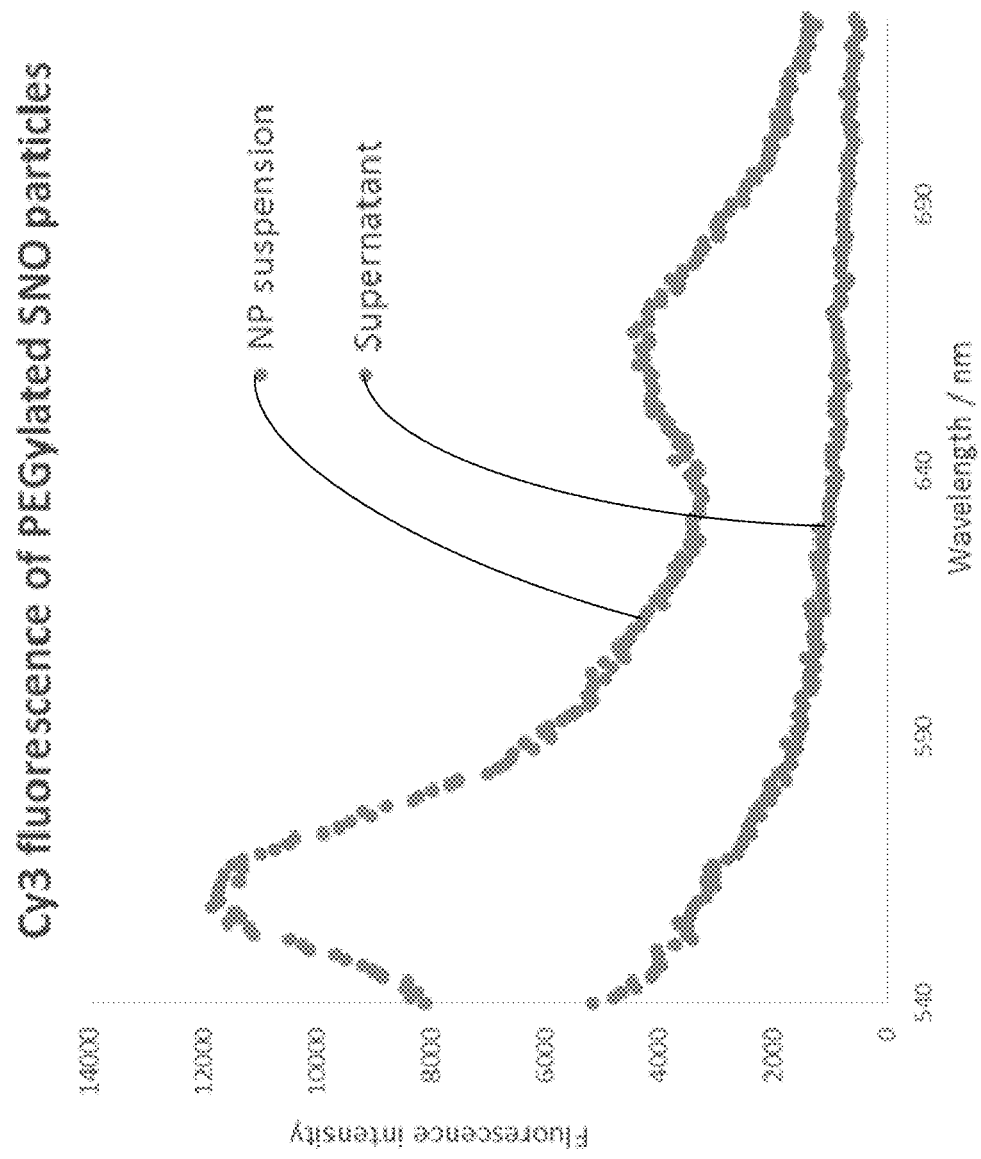
FIG. 7. Functionality of surface thiols allows for PEGylation via maleimide linkage, Cy3-PEG 3K, fluorescence maximum at 570 nm. Plots from top to bottom, respectively: NP suspension and Supernatant.

Functionality of surface thiols allows for PEG-ylation via maleimide linkage (Cy3-PEG 3K, fluorescence maximum at 570 nm) (FIG. 7).

Impact on release profiles from the doping of the empty/pre-loaded sol-gel monolith with small PEG chains (NACSNO, Curcumin, NO).

The effect of added PEG400 on release rates of NACSNO (SNO derivative of N-acetylcysteine) and curcumin from nanoparticles generated using the new block gel protocol (Universal Drug Delivery Platform).

New protocol in which NACSNO and curcumin are infused into a gel block prepared from TMOS using the standard Brinker method for gelation. Once the gel is loaded with the deliverables, the gel is lyophilized and then milled to produce the loaded nanoparticles.

Four separate gels are prepared for each of the deliverables

One gel has no added PEG whereas the other three have varying amounts of added PEG400. The percentage of added PEG shown in the figures refers to the percentage of PEG added compared to what was added in our original protocol.

Figure 8:
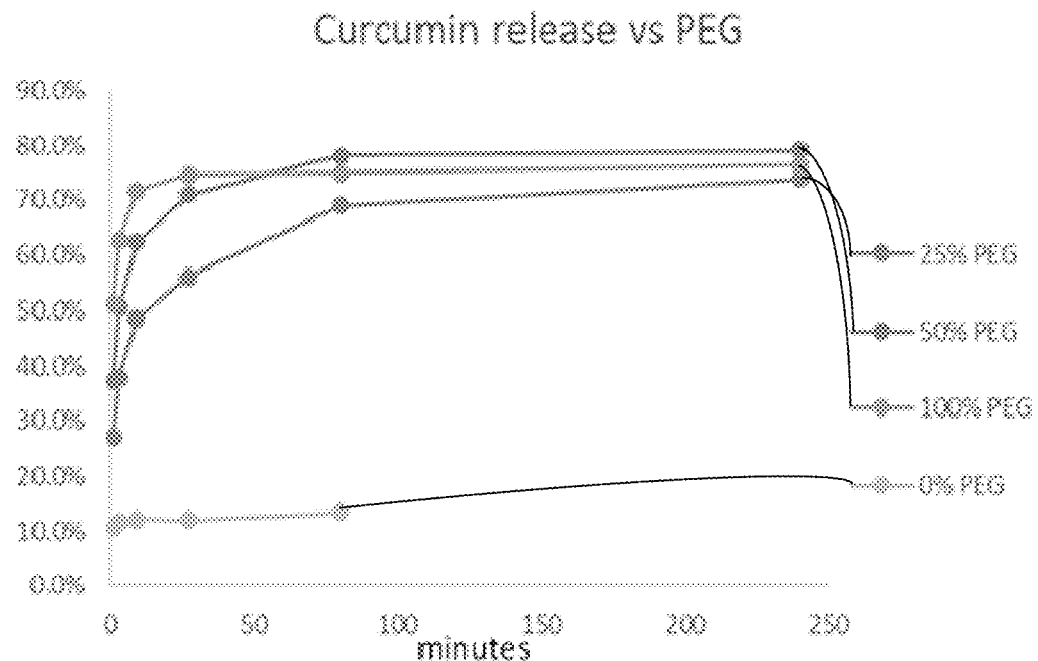
FIG. 8. Curcumin release at different amounts of PEG. Plots from top to bottom, respectively, at right side of plots: 50% PEG, 100% PEG, 25% PEG and 0% PEG.
Figure 9:
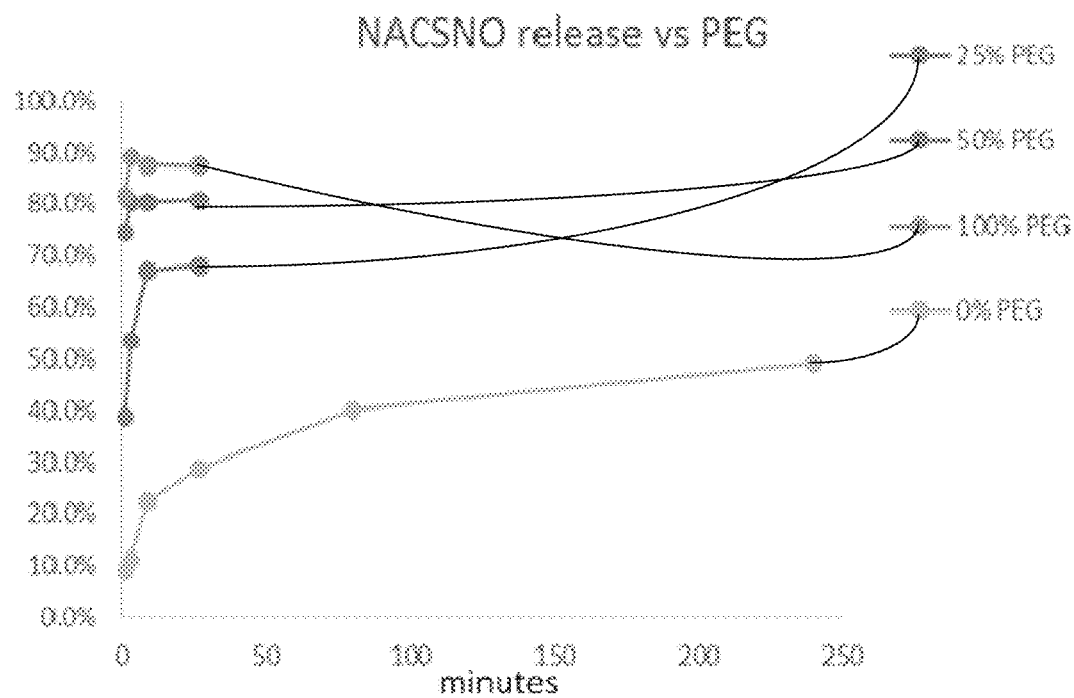
FIG. 9. NACSNO release at different amounts of PEG. Plots from top to bottom, respectively: 100% PEG, 50% PEG, 25% PEG and 0% PEG.

FIGS. 8 and 9 illustrate, respectively, curcumin release and NACSNO release at different amounts of PEG.

Fluorescence Imaging Showing PEG Halo Around SNO-np

The SNO nanoparticles were prepared with a fluorescent probe covalently attached within the interior matrix. Fluorescent labeled PEG was attached on the surface using maleimide derivatized fluorescent PEG to bind to the thiols attached to the nanoparticles. The two fluorescent probes emit different wavelengths. The results show that when the microscope monitors only the emission from the nanoparticle itself (seen as individual or clumbed bright spots) the image is much smaller than when the same image includes the signal from the PEG consistent with the PEG forming a halo around the PEGylated nanoparticles.

Impact of Silane Doping on the Release Profiles from the New UDDP Nanoparticle Platform Gel monoliths/blocks are formed using either the pure formulation with only TMOS (tetramethoxysilane), referred to Br1 (Brinker method for forming gels) or with TMOS doped with a trimethoxy silane with the fourth site either a thiol containing group (MPTS) of an alkyl side chain (octyl). The gels are allowed to fully form before loading with test molecules. Derivatized PEG chains (derivatized with maleimide, which rapidly binds to thiols) are attached to the fully formed nanoparticles that have been doped with MPTS (contains a thiol).

Figure 10:
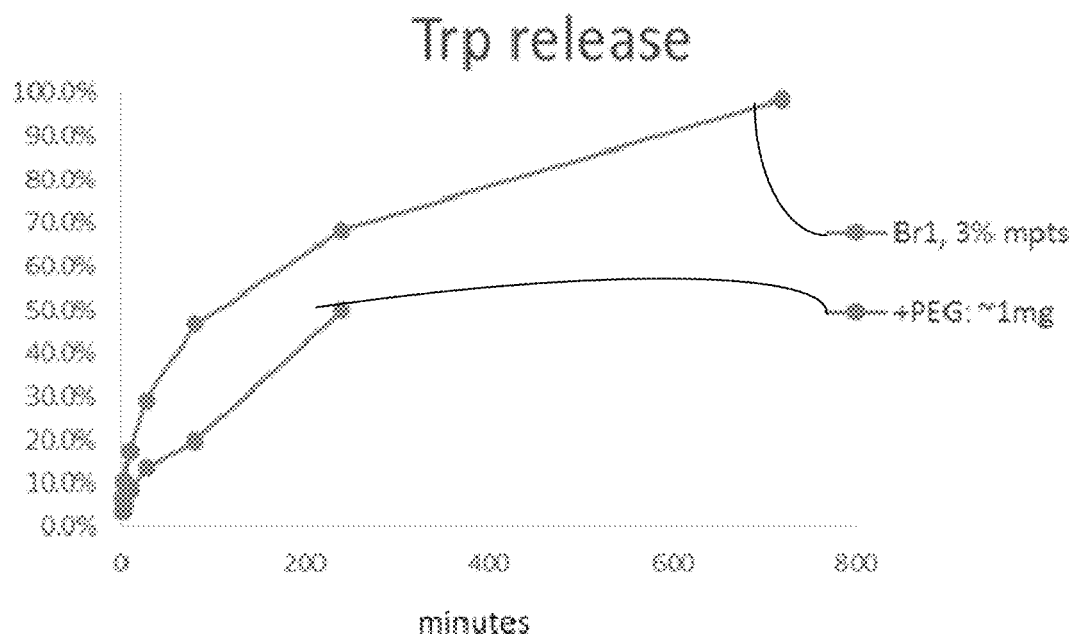
FIG. 10. Effect of surface PEGylation on release rate, suing Trp release as an example. Plots from top to bottom, respectively: Br1, 3% mpts and +PEG: ~1 mg.

Release Profile of Tryptophan from Nanoparticles with and without PEGylation (FIG. 10)

Results are similar to early studies on SNO-nps, curcumin loaded and NACSNO loaded nanoparticles showing that surface PEGylation slows release.

Figure 11:
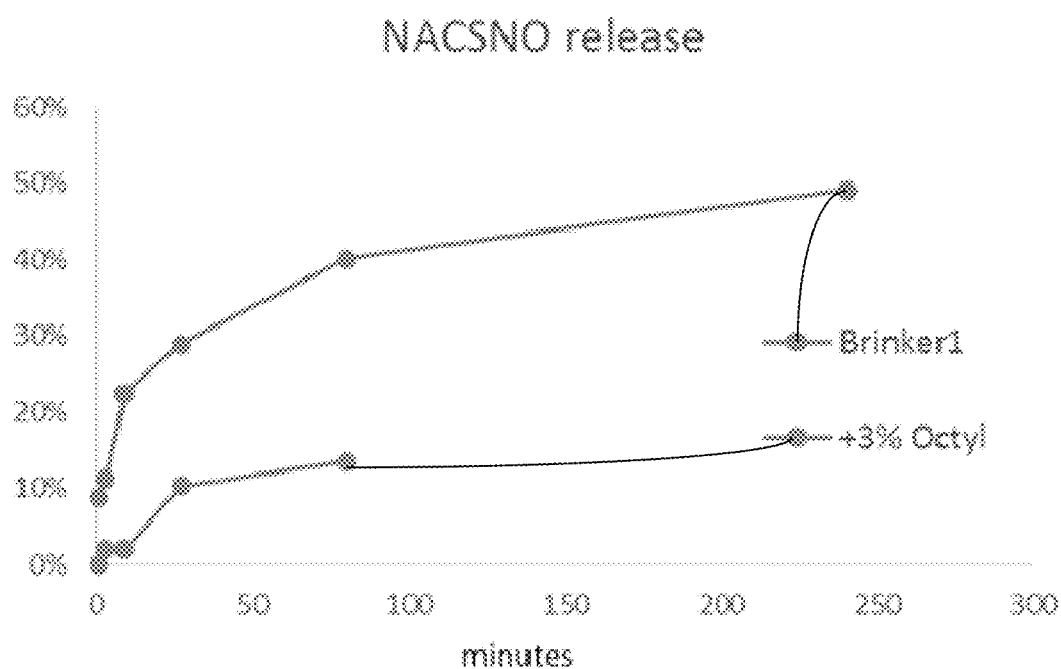
FIG. 11. Doping of gel with octyl-TMOS reduces release of NACSNO. Plots from top to bottom, respectively: Brinker 1 and +3% Octyl.
Figure 12:
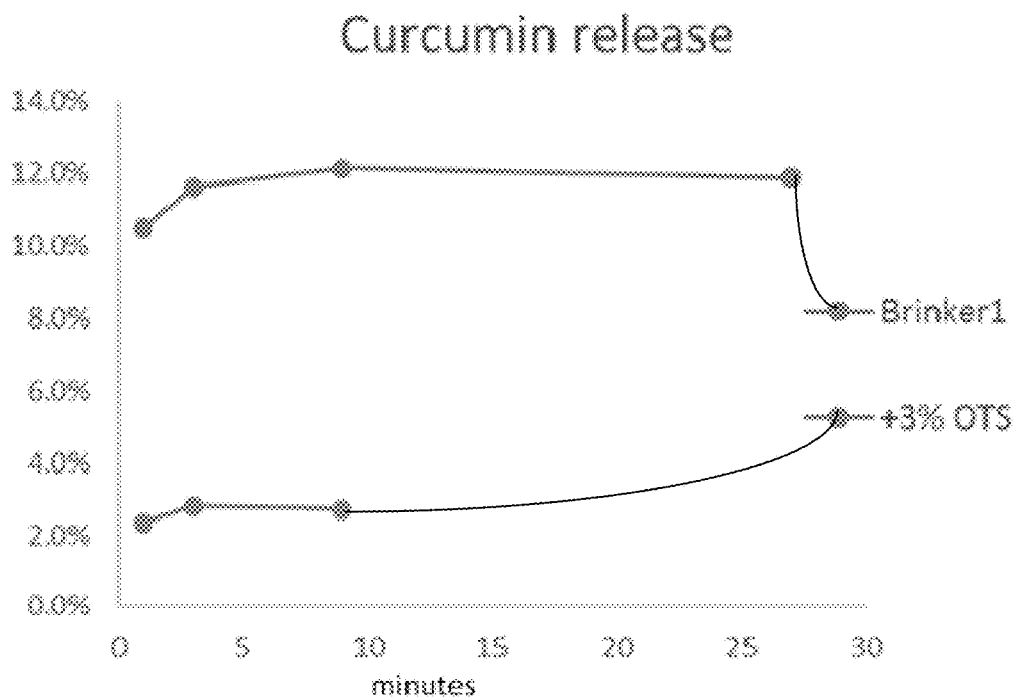
FIG. 12. Doping with Octyl-TMOS reduces release of curcumin from Br1. Plots from top to bottom, respectively: Brinker 1 and +3% Octyl.

Release of NACSNO (SNO-Derivative of N-Acetylcysteine) and Curcumin as a Function of Doping the Gel Block with an Octyl Group (FIG. 11)

The presence of the octyl group slows release of both the water soluble NACSNO and lipid soluble curcumin.

Figure 13:
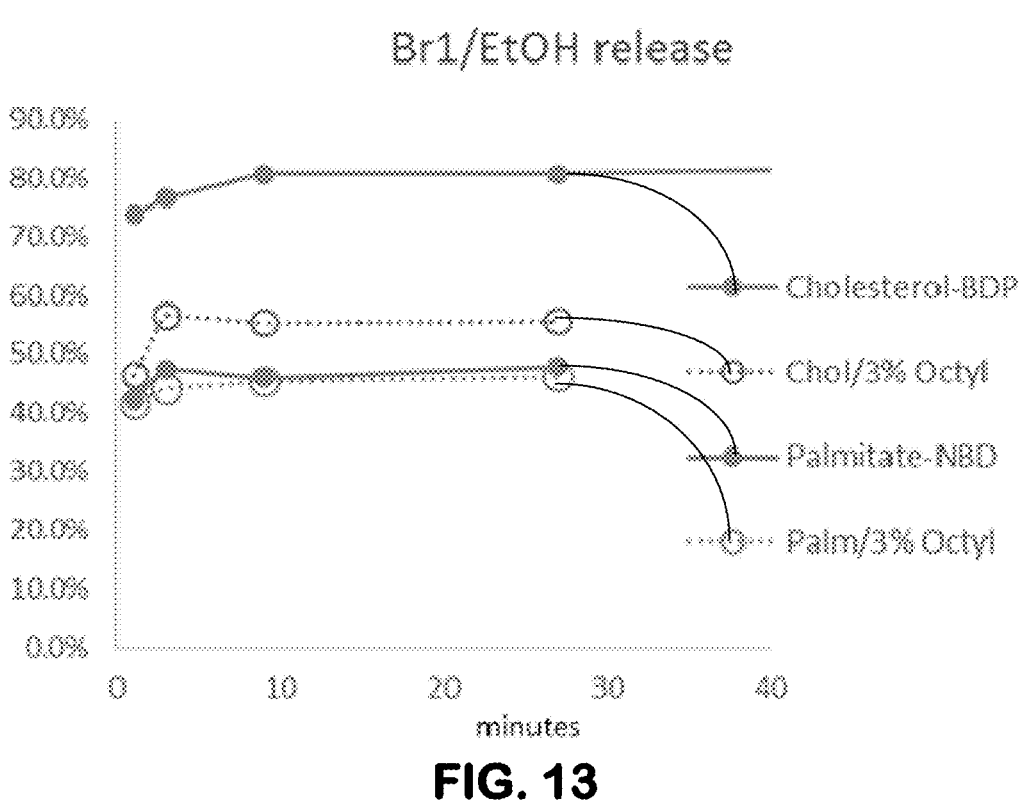
FIG. 13. Effects of doping del with 3% octyl-TMOS on release of lipids. Plots from top to bottom, respectively: Cholesterol-BDP, Chol/3% Octyl, Palmitate-NBD, and Palm/3% Octyl.
Figure 14:
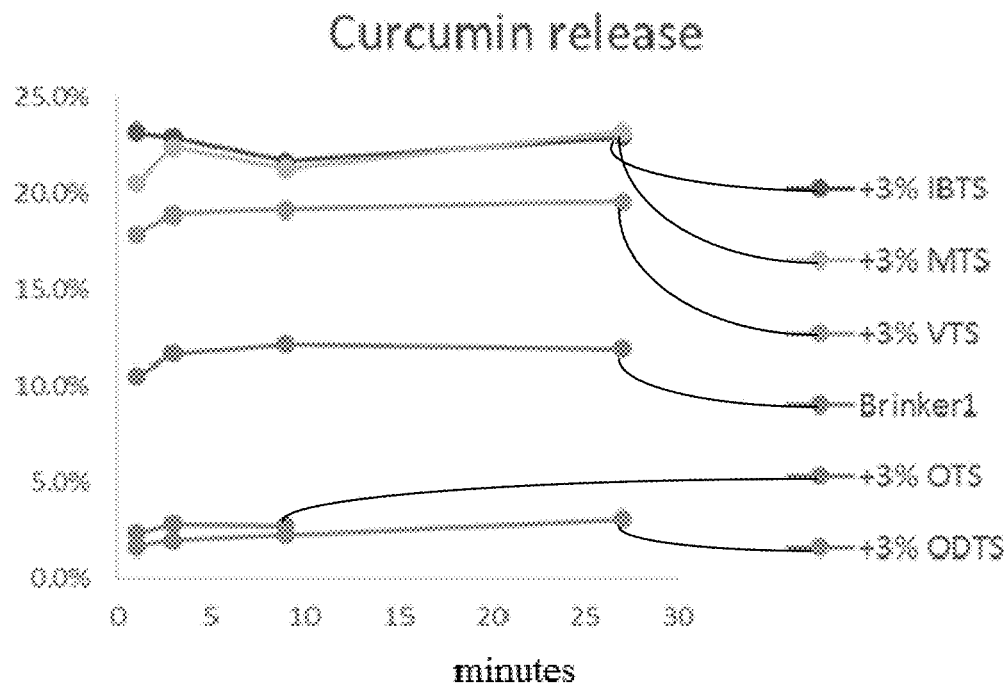
FIG. 14. Doping affects curcumin release. Plots from top to bottom, respectively, at left side of plots: +3% IBTS, +3% MTS, +3% VTS, Brinker1, +3% OTS, and +3% ODTS.
Figure 15:
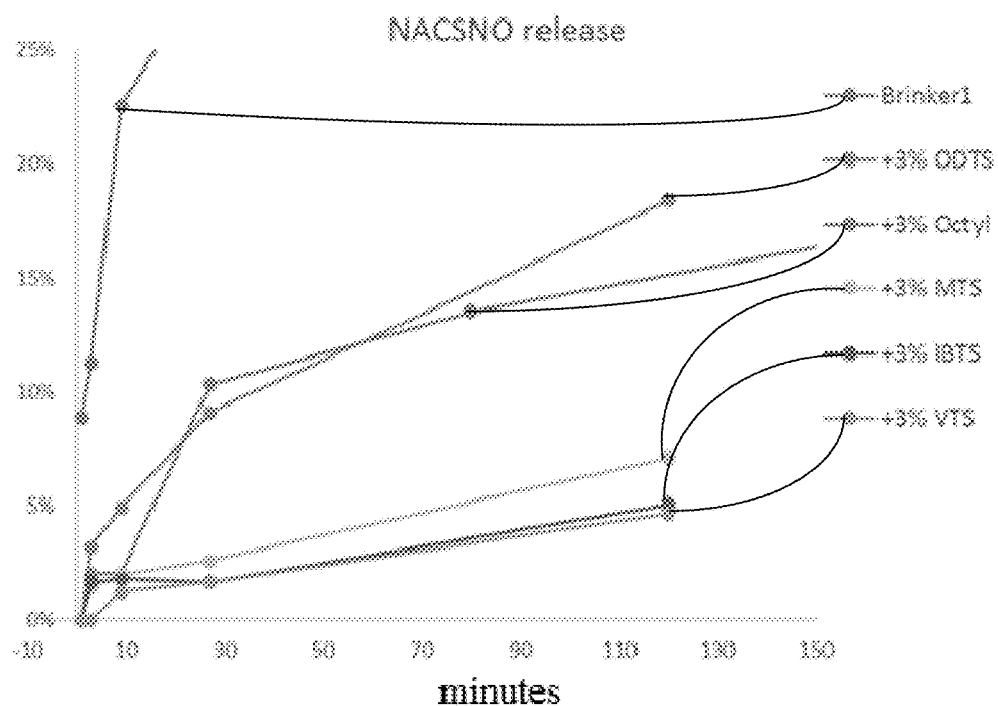
FIG. 15. Doping affects NACSNO release. Plots from top to bottom, respectively, at right side of plots: Brinker1, +3% ODTS, +3% Octyl, +3% MTS, +3% IBTS and +3% VTS.

Effects of Doping Del with 3% Octyl-TMOS on Release of Lipids (FIG. 13)

3% octyl doped gel changed cholesterol release(from 80% released down to 55% released), but had no effect on palmitate release.

Impact of Silane Doping on Release Profiles

Empty sol-gel monoliths/blocks are formed using either the pure formulation with only TMOS (tetramethoxysilane), referred to Br1 (Brinker method for forming gels) or with TMOS doped with a trimethoxy silane with the fourth site either: a thiol containing group (e.g. MPTS) of an alkyl side chain; an amine containing group of an alkyl side chain (e.g. APTS); alkyl side chains of varying length.

Other potential dopants (X-trimethoxy silanes) with X being: PEG chain, lipids/fatty acids, carboxyl containing alkyl chain, sugar or starch containing alkyl chain.

Tuning the nanoparticle release profiles of curcumin and S-nitrosoN-acetylcysteine (NACSNO) by doping the gel with trimethoxysilanes with different size/shaped alkyl side chains and with a thiol containing trimethoxysilane (MPTS): Thiol-MPTS, Isobutyl-IBTS, Vinyl-VTS, Octyl-OTS Octadecyl-ODTS, Undoped basic formulation Brinker 1.

pH can be Used to Control the Release Rates pH is known to influence the rate of gelation and the pore structure. High pH accelerates gelation time but creates sol-gels with larger pores. Low pH slows gelation and favors a compact polymer structure if small pores. Addition of base to the initial mixture results in faster gelation and faster release profiles for deliverables loaded after gelation. The added base or acid is rinsed out once the sol-gel monolith is formed thus eliminating concerns of how pH might degrade specific deliverables.

Figure 16:
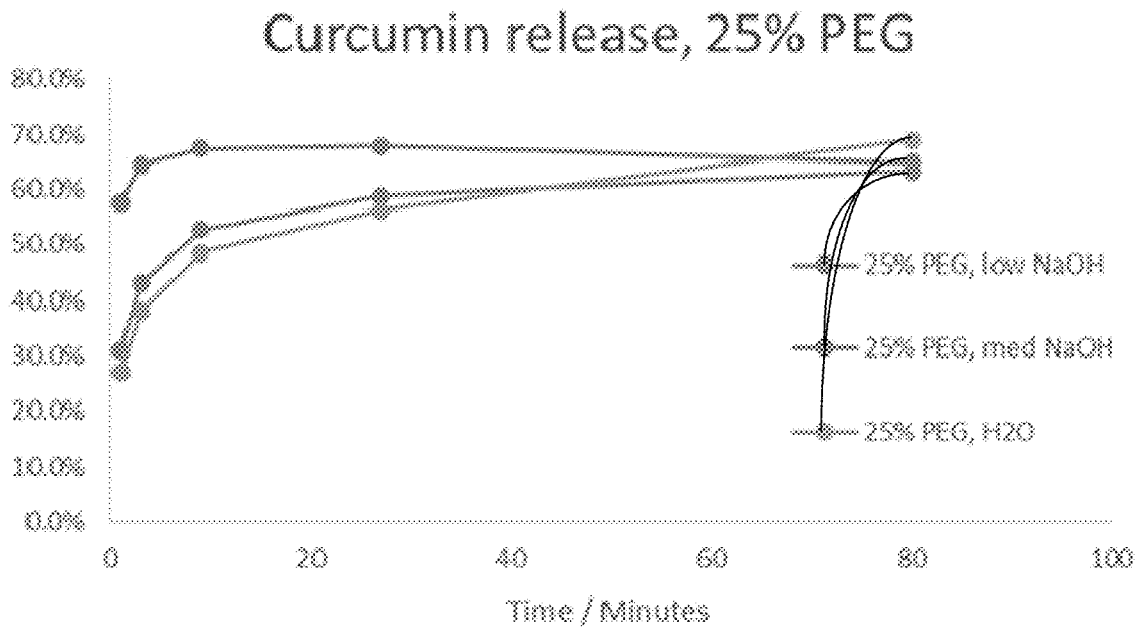
FIG. 16. Release rate of curcumin in ethanol increases as gelation pH is increased. Release rate of curcumin in ethanol increases as pH is increased in the condensation step for a PEG400 doped Br Sol-gel. Curcumin is added after the sol-gel is formed. Plots from top to bottom, respectively, at left side of plots: 25% PEG, med NaOH; 25% PEG, low NaOH; and 25% PEG, H$_2$O.
Figure 17:
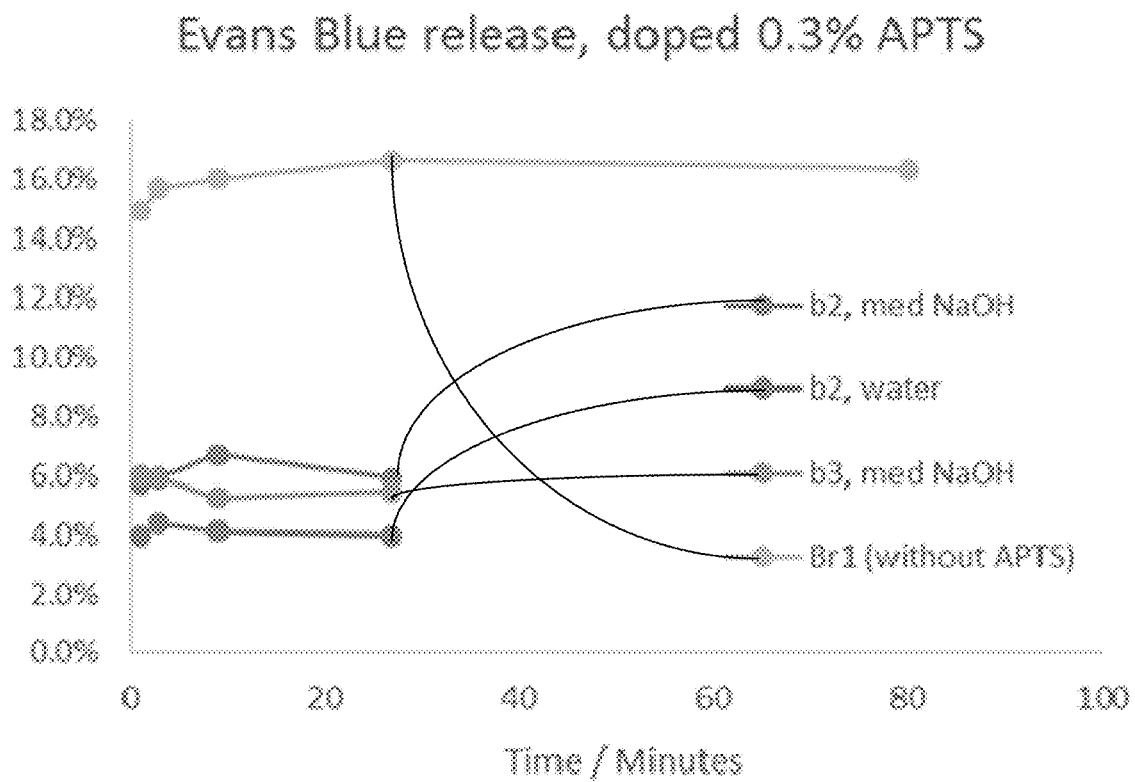
FIG. 17. APTS doped Br sol-gels holds Evans Blue in particle matrix likely via sulfonate—amine salt bridge. Plots from top to bottom, respectively, at right side of plots: Br1 (without APTS); b2, med NAOH; b3, med NaOH; and b2, water.
Figure 18A:
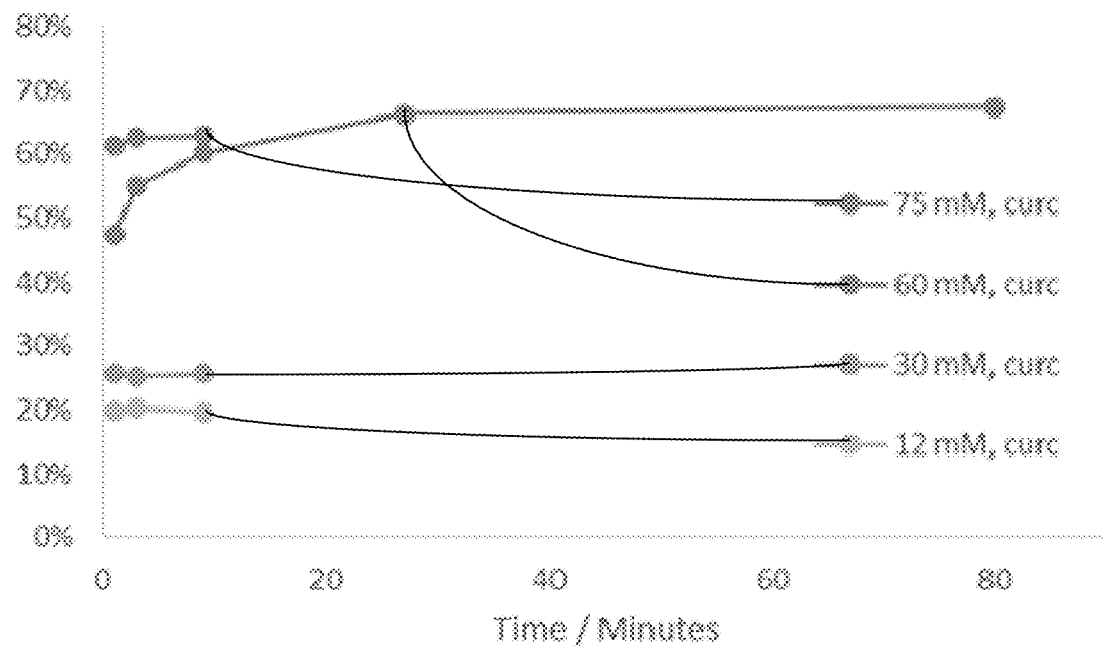
FIGS. 18A-18B. Curcumin (A) and (B) Evans Blue APTS doped gels. The gels were doped with 0.3% APTS. Rate of condensation changed by mM NaOH concentration (75, 60, 30, 12) added prior to condensation step. Increasing gel times for decreasing amount of added NaOH: (2 mins, 30 mins, 15 hours, 1.5 days: 75, 60, 30, 12 mM NaOH). Curcumin release in ethanol; Evans blue release in water. Both plots from top to bottom, respectively, at left side of plots: 75 mM, 60 mM, 30 mM and 12 mM.
Figure 18B:
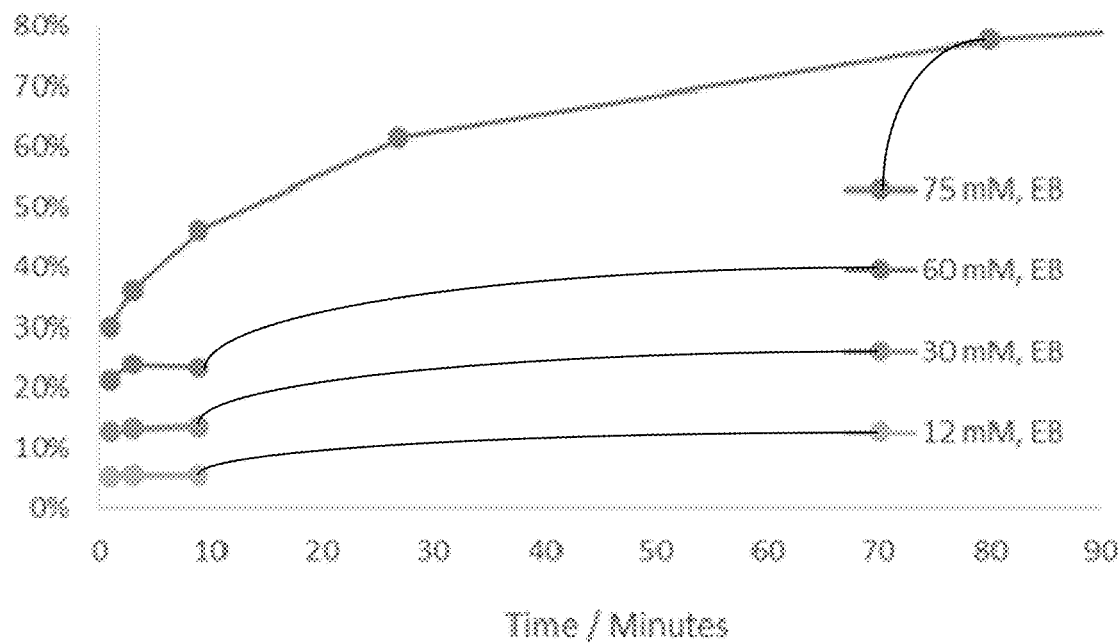
Figure 19A:
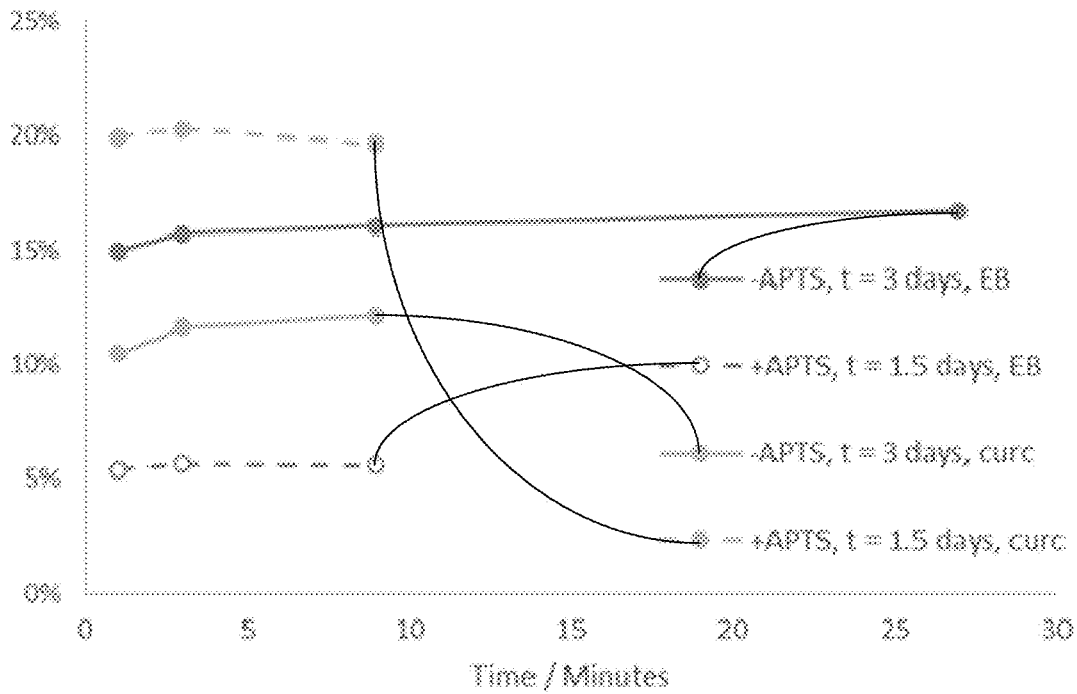
FIGS. 19A-19C. Comparison of gels with and without APTS. (A) Slow gel. Both gels took >1 day to form, thus have fine porous structure. +APTS slows Evans blue release; curcumin release is increased. (B) Medium gel. Both gels took about 1 hour to form, thus have medium porous structure. (C) Fast gel. Release profile for Evans Blue: Comparison of fast forming gels with and without APTS. Both gels took about 2 minutes to form, thus have open porous structure. The differences are attributed to the stabilization imparted by the positive charge from the amine groups. (A) Plots from top to bottom, respectively: +APTS, t=1.5 days, curc; –APTS, t=3 days, EB; –ATPS, t=3 days, curc; and +ATPS, t=1.5 days, EB. (B) Plots from top to bottom, respectively, at right side of plots: –APTS, t=1 hr, EB; +APTS, t=½ hr, curc; –ATPS, t=1 hr, curc; and +ATPS, t=½ hr, EB.
Figure 19B:
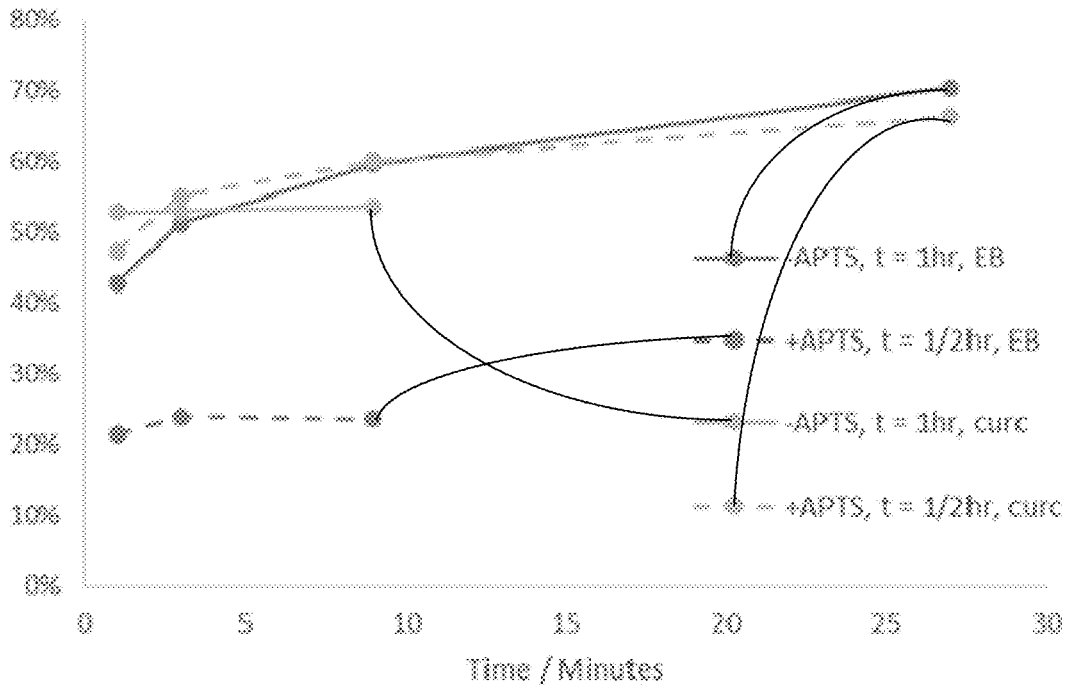
Figure 19C:
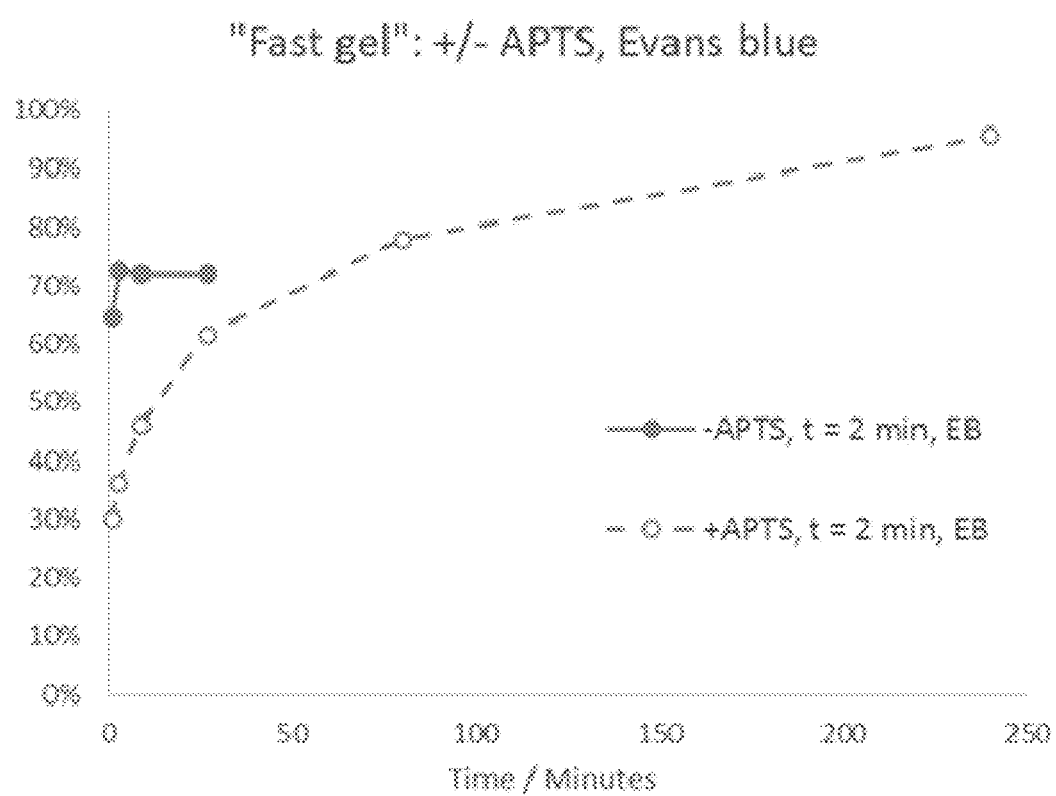
Figure 20:
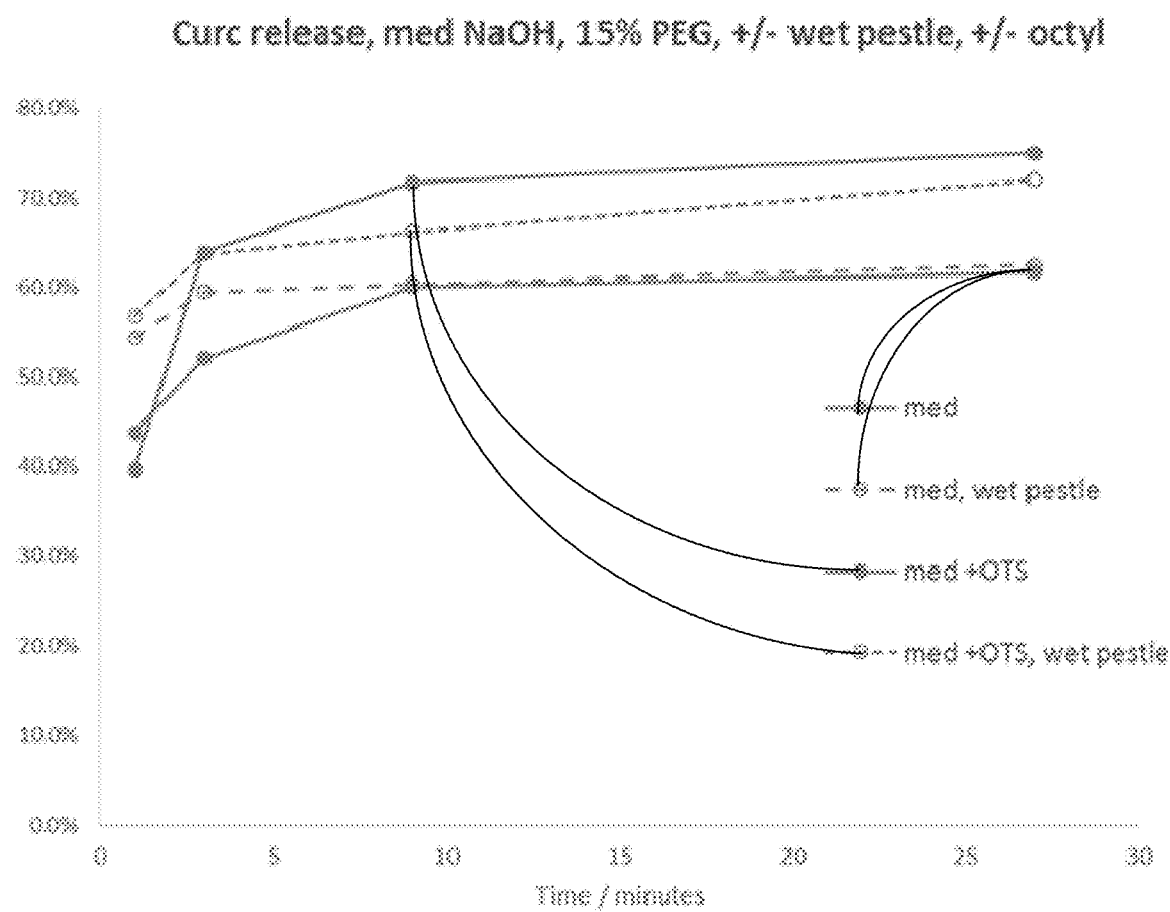
FIG. 20. Curcumin release, med NaOH, 15% PEG, +/–wet pestle, +/–octyl. Plots from top to bottom, respectively, at right side of plots: med+OTS; med+OTS, wet pestle; med, wet pestle; and med.
Figure 21:
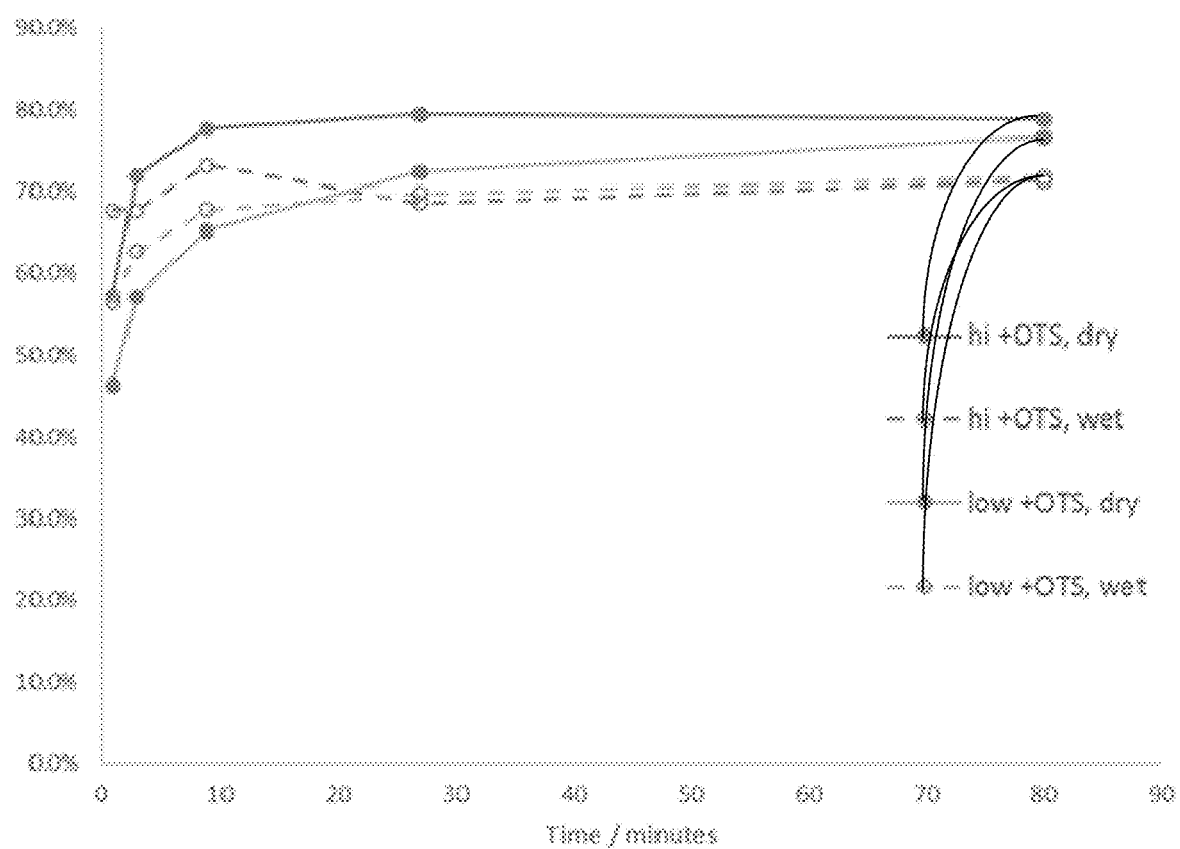
FIG. 21. Curcumin release, octyl doped, 15% PEG, +/–wet pestle. Plots from top to bottom, respectively, at right side of plots: hi+OTS, dry; low+OTS, dry; low+OTS, wet; and hi+OTS, wet.
Figure 22:
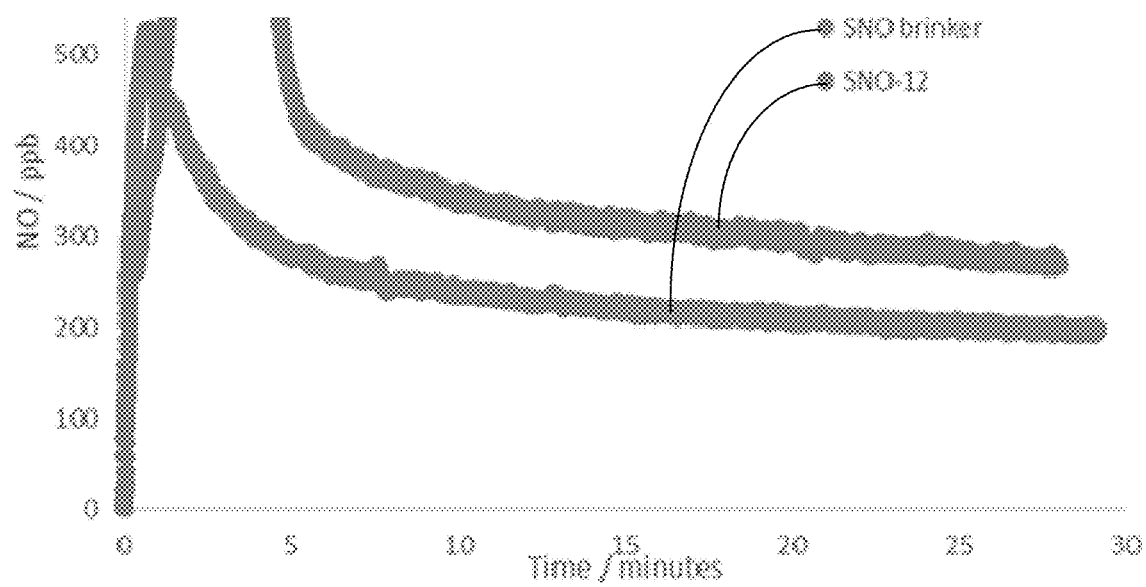
FIG. 22. SNO "original" vs "brinker" NO release. SNO-12 (1.43 umole thiol/mg); 40:60 MPTS:TMOS; 60% (w) PEG; 29% efficiency (released NO/thiol). SNO-Brinker (1.31 umole thiol/mg); 20:80 MPTS:TMOS; 15% (w) PEG; 23% efficiency (released NO/thiol). Plots from top to bottom, respectively, at right side of plots: SNO-12 and SNO brinker.
Figure 23:
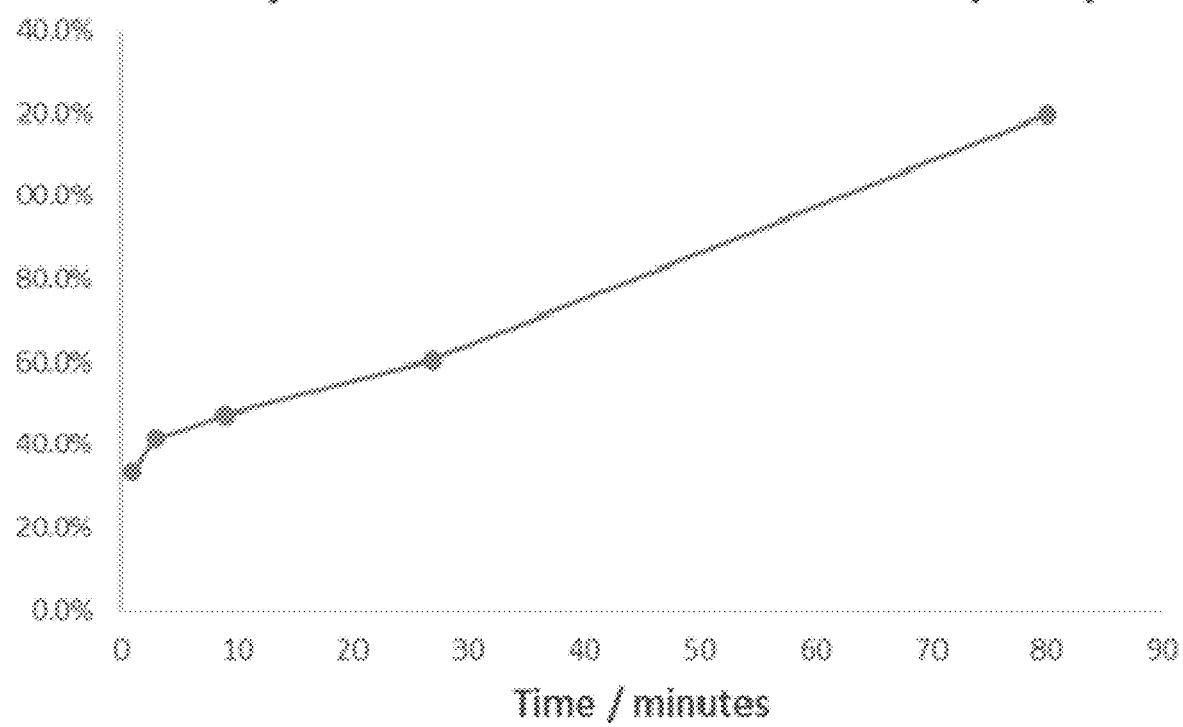
FIG. 23. Naproxen release from new protocol nanoparticles. Naproxen is weakly soluble in water hence the slow release in methanol indicates very slow release for water.

Increasing pH increases release of curcumin (FIG. 16). Curcumin series shows that in a sol-gel doped with 25% PEG400, increasing amount off base added for the initial condensation step, will increase the release rate of the loaded curcumin.

Incorporation of Covalently Attached Amine Groups (Via APTS), the Release Rate of the Negatively Charged Evans Blue Dye is Substantially Slowed Amines are incorporated by mixing hydrolyzed APTS with hydrolyzed TMOS. The resulting sol-gel monolith is loaded with the water soluble dye Evans Blue which has four negatively charged groups. Without amine doping the release of Evans Blue is near instantaneous when the particles are added to water. The presence of the amines substantially slows release.

In APTS doped sol-gels, the release time is enhanced by increasing the pH. Release profiles for Evans Blue and Curcumin in Br sol-gels doped with APTS show an increase in release with increasing addition of base to the initial mixture prior to condensation. The deliverables are added after sol-gel formation. Increasing pH accelerates gelation time.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of preparing deliverable-containing particles comprising a deliverable, the method comprising:
   preparing a solution having a pH of less than or equal to 3, the solution comprising at least one silane dissolved in at least one solvent, wherein the solvent comprises at least one alcohol;
   raising the pH of the solution and adding water to the solution to form a hydrogel, wherein the hydrogel comprises silanes linked to form at least one monolith network;
   loading the hydrogel with at least one deliverable to form a deliverable-loaded hydrogel;
   drying the deliverable-loaded hydrogel to form a dried material; and
   milling the dried material to form a plurality of deliverable-containing particles,
   wherein said loading the hydrogel with the at least one deliverable is conducted after the hydrogel has been formed and before said drying.

2. The method of claim 1, wherein said milling the dried material comprises wet milling to form a slurry comprising the plurality of deliverable-containing particles.

3. The method of claim 1, wherein the method further comprises adding to the plurality of deliverable-containing particles one or more materials selected from the group consisting of polyethylene glycol materials, anions, cations, and alkanes.

4. The method of claim 1, wherein the solvent comprises methanol having a concentration of 25% to 75% by weight in the solution.

5. The method of claim 1, wherein the solvent comprises methanol having a concentration of 40% to 50% by weight in the solution.

6. The method of claim 1, wherein preparing the solution comprises incubating the solution at a temperature of about 60 degrees C.

7. The method of claim 1, wherein the at least one silane comprises a substituted silane, wherein the substituted silane is substituted with at least a first PEG group having a molecular weight in the range of from about 200 Daltons to about 10K Daltons.

8. The method of claim 7, wherein at least one targeting molecule comprising at least one peptide, antibody, or imaging agent is attached to the first PEG group.

9. The method of claim 1, wherein said loading the hydrogel with the at least one deliverable comprises forming a solution comprising the at least one deliverable, and contacting the solution comprising the at least one deliverable with the hydrogel.

10. The method of claim 9, wherein the at least one deliverable comprises one or more compounds selected from curcumin, S-nitrosothiol derivative of N-acetyl cysteine (NACSNO), nitric oxide (NO).

11. A deliverable-containing particle formed by the method recited in claim 1.

12. A method of treating a subject with a disease or disorder, the method comprising administering to the subject a therapeutically effective amount of a deliverable-containing particle formed by the method recited in claim 1.

13. The method of claim 1, wherein the at least one deliverable comprises at least one compound that is hydrophobic and that has a molecular weight of less than 500 grams per mole.

14. The method of claim 1, wherein the deliverable-containing particles comprise micron-sized particles.

15. A method of preparing deliverable-containing particles comprising a deliverable, the method comprising:
- preparing a solution having a pH of less than or equal to 3, the solution comprising at least one silane dissolved in at least one solvent, wherein the solvent comprises at least one alcohol;
- raising the pH of the solution and adding water to the solution to form a hydrogel, wherein the hydrogel comprises silanes linked to form at least one monolith network;
- loading the hydrogel with at least one deliverable to form a deliverable-loaded hydrogel;
- drying the deliverable-loaded hydrogel to form a dried material; and
- milling the dried material to form a plurality of deliverable-containing particles,
- wherein said loading the hydrogel with the at least one deliverable is conducted after the hydrogel has been formed and before said drying, to achieve a loading of the at least one deliverable (1) that is at least 5 weight percent based on the total mass of the deliverable-containing particles, and (2) that is greater than the weight percent that would be achieved by loading the hydrogel with the at least one deliverable before said raising the pH of the solution.

16. The method of claim 15, wherein the solvent comprises methanol having a concentration of 25% to 75% by weight in the solution.

17. The method of claim 15, wherein the at least one deliverable comprises at least one compound that is hydrophobic and that has a molecular weight of less than 500 grams per mole.

18. The method of claim 15, wherein the gel takes greater than one day to form, whereby the porosity of the deliverable-containing particles is finer than would be obtained with a gel that forms in about one hour.

19. A deliverable-containing particle formed by the method recited in claim 15.

20. The method of claim 15, wherein the deliverable-containing particles comprise micron-sized particles.

21. The method of claim 15, wherein the at least one silane comprises at least one compound selected from the group consisting of tetramethoxy silane, tetraethoxy silane, X-trimethoxy silanes, and X-triethoxy silanes, wherein X is selected from among thiols, amines, alkyl chains, fatty acids, carboxy groups, carbonyl groups, PEG chains, sugars, starches, and peptides;
- at least one deliverable is hydrophobic and has a molecular weight of less than 500 grams per mole; and
- the gel takes greater than one day to form, whereby the porosity of the deliverable-containing particles is finer than would be obtained with a gel that forms in about one hour.

22. A deliverable-containing particle formed by the method recited in claim 21.

* * * * *